United States Patent
Bailly et al.

(10) Patent No.: US 11,759,303 B2
(45) Date of Patent: Sep. 19, 2023

(54) KITS FOR SURGICAL REPAIR OF SOFT TISSUE DEFECTS AND COMPONENTS, PACKAGING, AND METHODS OF USE THEREOF

(71) Applicant: SOFRADIM PRODUCTION, Trevoux (FR)

(72) Inventors: Pierre Bailly, Caluire-et-Cuire (FR); Thierry Brune, Jarnioux (FR); Guy Jouvray, Pierre Chatel (FR)

(73) Assignee: SOFRADIM PRODUCTION, Trevoux (FR)

( * ) Notice: Subject to any disclaimer, the term of this patent is extended or adjusted under 35 U.S.C. 154(b) by 152 days.

(21) Appl. No.: 17/202,162

(22) Filed: Mar. 15, 2021

(65) Prior Publication Data
US 2021/0330438 A1 Oct. 28, 2021

(30) Foreign Application Priority Data
Apr. 23, 2020 (EP) .................................... 20315214

(51) Int. Cl.
*A61F 2/00* (2006.01)

(52) U.S. Cl.
CPC .... *A61F 2/0063* (2013.01); *A61F 2002/0072* (2013.01); *A61F 2220/0075* (2013.01)

(58) Field of Classification Search
CPC .......... A61F 2/0063; A61F 2/011; A61F 2/95; A61F 2/2427; A61F 2/2466; A61F 2002/0072; A61F 2220/0075; A61F 2/01; A61F 2/02
See application file for complete search history.

(56) References Cited

U.S. PATENT DOCUMENTS

| | | | |
|---|---|---|---|
| 5,397,332 A | 3/1995 | Kammerer et al. | |
| 5,464,403 A | 11/1995 | Kieturakis et al. | |
| 9,655,709 B2 * | 5/2017 | Kelly | A61F 2/0063 |
| 10,028,814 B2 * | 7/2018 | Levin | A61F 2/0063 |
| 2006/0009802 A1 * | 1/2006 | Modesitt | A61B 17/0057 606/215 |
| 2008/0195121 A1 * | 8/2008 | Eldar | A61F 2/0063 606/151 |
| 2011/0040311 A1 * | 2/2011 | Levin | A61B 17/0469 606/151 |

(Continued)

FOREIGN PATENT DOCUMENTS

| | | |
|---|---|---|
| EP | 0625334 A1 | 11/1994 |
| WO | 2013020107 A1 | 2/2013 |

OTHER PUBLICATIONS

Extended European Search Report issued in European Patent Application No. 21170306.1 dated Aug. 16, 2021.

(Continued)

*Primary Examiner* — Erich G Herbermann
(74) *Attorney, Agent, or Firm* — WEBER ROSSELLI & CANNON LLP

(57) ABSTRACT

The present disclosure describes kits for surgical repair of soft tissue defects, including hernias. The kits include any combination of components selected from an implantable sheet, a central tie, a delivery tool, a delivery tool insert configured to be received within the delivery tool, a rolling device, and an insertion member. Packaging for the kits and/or components and methods of using the kits and/or components are also provided.

14 Claims, 24 Drawing Sheets

(56) References Cited

U.S. PATENT DOCUMENTS

2013/0018395 A1\* 1/2013 Friedlander .......... A61F 2/0063
606/151
2013/0310637 A1 11/2013 Iceman et al.

OTHER PUBLICATIONS

Extended European Search Report issued in European Application No. 20315214.5 dated Oct. 22, 2020.

\* cited by examiner

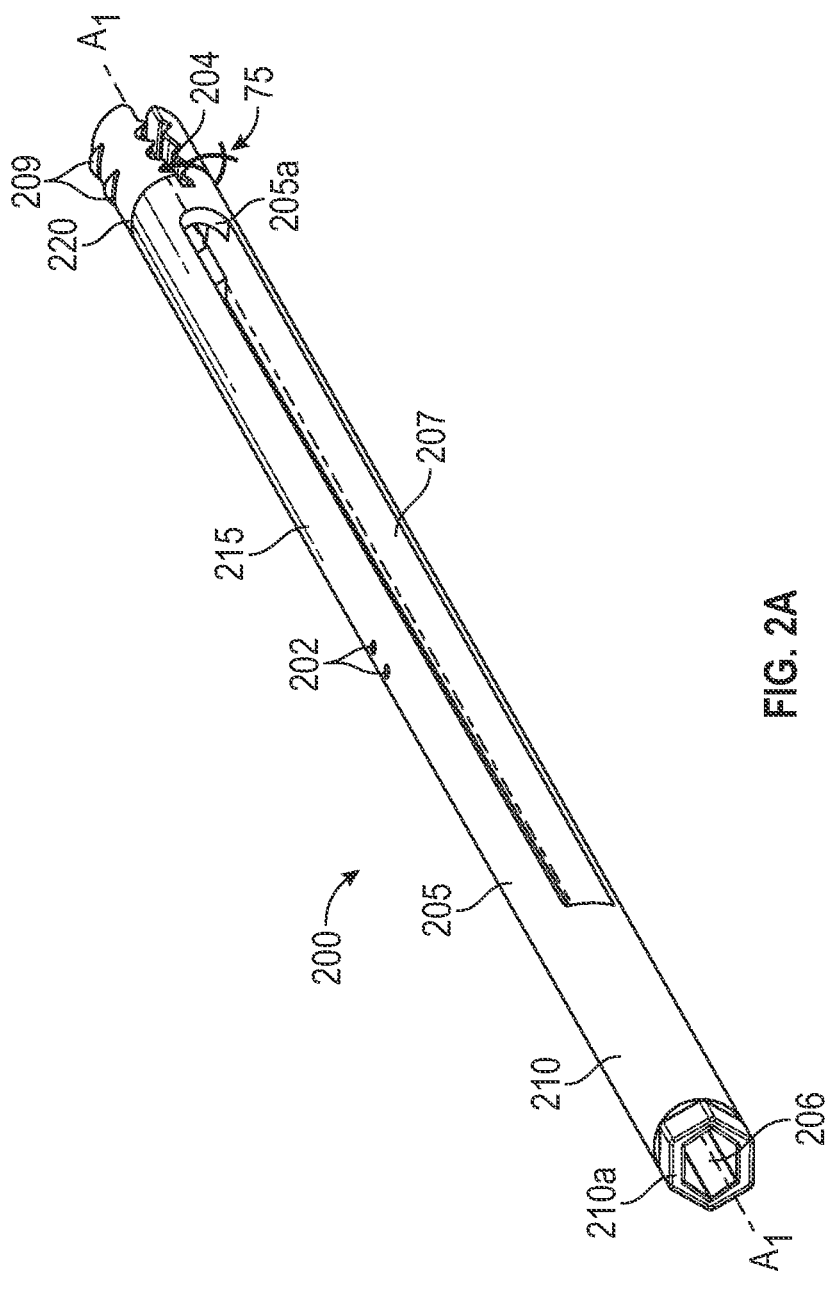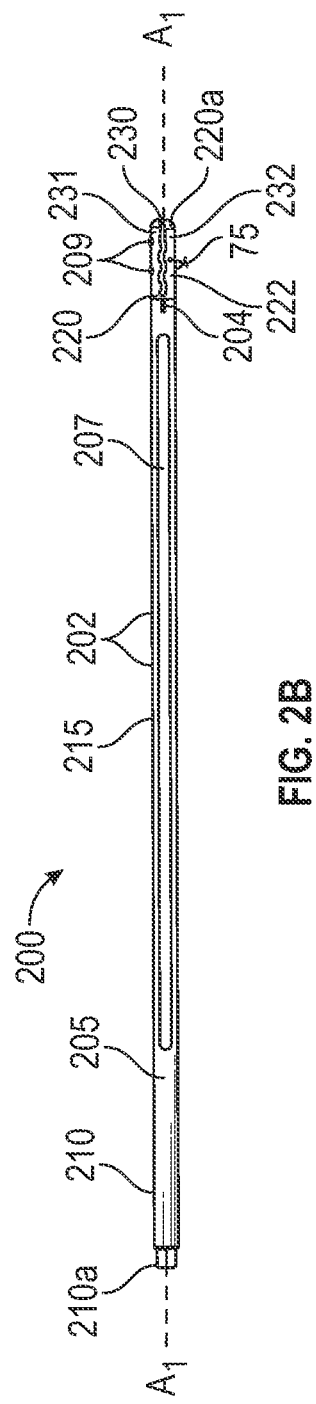
FIG. 2A
FIG. 2B

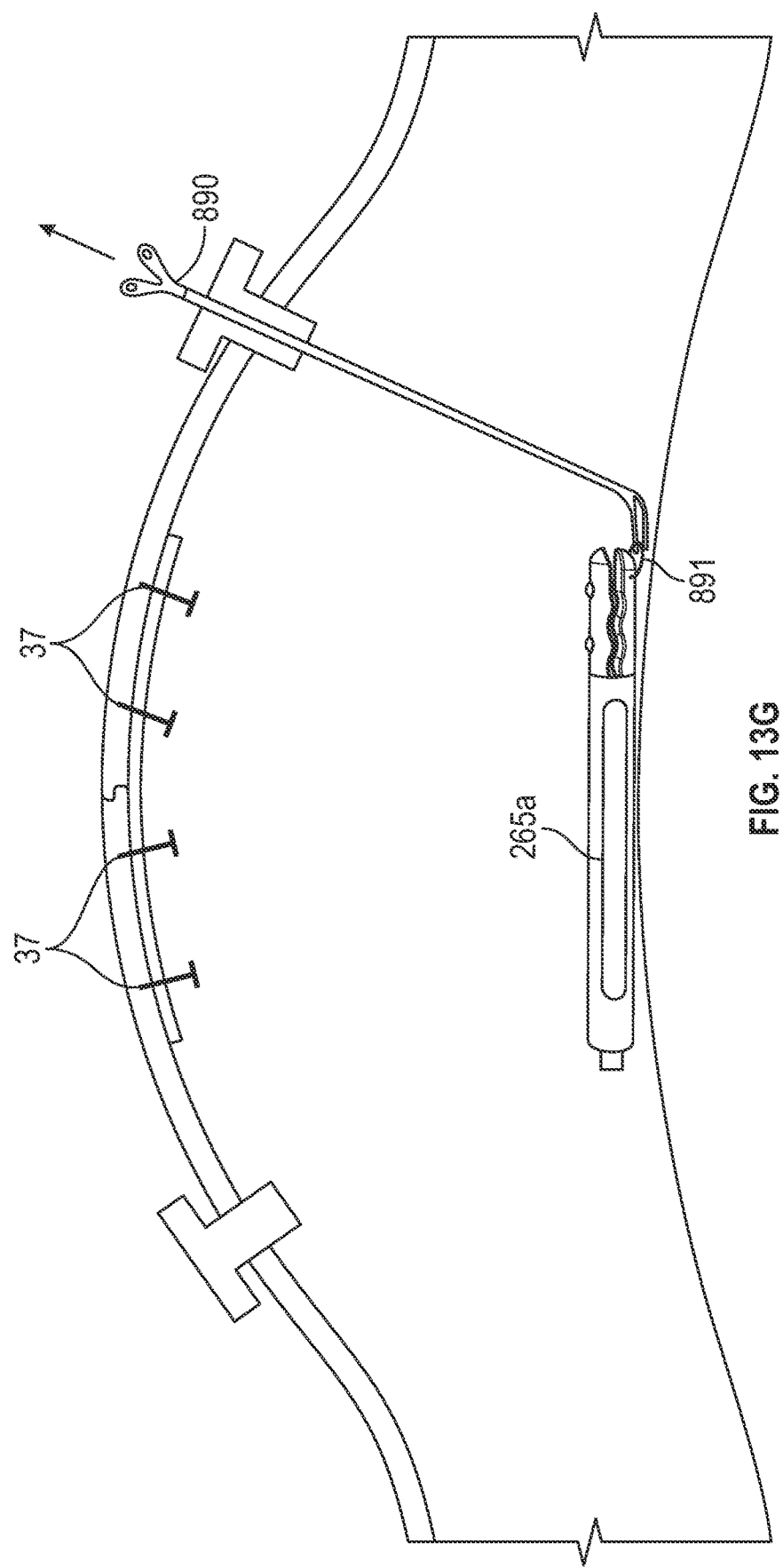

KITS FOR SURGICAL REPAIR OF SOFT TISSUE DEFECTS AND COMPONENTS, PACKAGING, AND METHODS OF USE THEREOF

CROSS-REFERENCE TO RELATED APPLICATIONS

This application claims the benefit of and priority to European Patent Application Number 20315214.5 filed on Apr. 23, 2020, the disclosure of the above-identified application is hereby incorporated by reference in its entirety.

TECHNICAL FIELD

The present disclosure describes kits for surgical repair of soft tissue defects, including hernias, and particularly to the components, packaging, and methods of use of such kits.

BACKGROUND

Various prosthetic repair materials are employed by surgeons for soft tissue repair including the repair of anatomical defects such as tissue and muscle hernias. For example, a ventral hernia in the abdominal wall is commonly repaired using an implantable sheet of biocompatible fabric, such as a knitted mesh (PARIETEX™, VERSATEX™, and the like) or a composite fabric that includes a mesh and an adhesion resistant barrier (SYMBOTEX™, PARIETENE™, and the like). The fabric is typically sutured, stapled, tacked, glued, or otherwise provisionally anchored in place over, under or within the defect. Tissue integration with the fabric, such as tissue ingrowth into and/or along the mesh fabric, eventually completes the repair. An implantable sheet of adhesion resistant barrier material, if provided alone or in combination with a fabric, prevents the growth of fibrous adhesions between the bowel (and other organs located in the abdominal cavity) and the sheet or fabric, specifically when the sheet is implanted inside the abdominal cavity (i.e. under the defect).

Various surgical techniques may be employed for soft tissue repair, including open or laparoscopic procedures. In addition, these surgical techniques may be performed directly by surgeon or with the assistance of a surgical robot. During a laparoscopic procedure, the prosthetic fabric may be routed, directly by the surgeon or with the assistance of a surgical robot, to the surgical site through a slender laparoscopic or robotic cannula. The fabric is typically collapsed, such as by rolling or folding, into a reduced configuration to facilitate its passage through the narrow cannula. Certain repairs, such as laparoscopic repair of ventral hernias, may require large sheets of prosthetic fabric that may be difficult to deliver laparoscopically, as well as difficult to properly deploy, orientate, position, or fixate following delivery.

Preparation and/or delivery of the prosthetic fabric can critically impact later steps of the surgical procedure. In laparoscopic procedures, prosthetic fabrics are typically prepared and delivered into a small operating space. This can make the deployment, orientation, positioning, and/or fixating of the fabric more difficult and more time consuming. It can also require the surgeon to dedicate one hand to simply trying to maintain the fabric in a certain position while the surgeon's second hand is trying to fixate the fabric in the tissue. This can be particularly challenging since the edges of the fabrics tend to bend or fold inside the small workspace. Mispositioning of the fixated prosthetic fabric can potentially lead to hernia recurrence.

It is an object of the present disclosure to provide kits and/or components of a kit which are designed to make preparation, insertion, deployment, orientation, positioning, and/or fixation of an implantable sheet easier, more intuitive and less time-consuming thereby rendering the surgical procedure more efficient and more effective.

It is another object of the present disclosure to provide kits and/or components of a kit which are designed to be prepared or delivered in a manner which allows a surgeon, directly or with the assistance of a surgical robot, to dedicate multiple hands to handle, deploy, orientate, position, and/or fixate the implantable sheet, during a standard laparoscopic or a robotically assisted ventral hernia repair.

SUMMARY

Surgical kits for soft tissue defect repair are described herein. The surgical kits include a combination of components selected from an implantable sheet, a central tie, a delivery tool, a delivery tool insert, a rolling device, and an insertion member. The delivery tool and delivery tool insert are configured to be combined to form a two-piece delivery device.

In embodiments, the delivery tool includes a flexible rod having an elongate body extending between a proximal end portion and a distal end portion, the elongate body including a lumen extending therethrough and at least one window defined within a sidewall of the elongate body. The window is configured to allow access to the lumen from outside the elongate body. The window is also configured to receive the at least one resilient arm of a delivery tool insert. The distal end portion includes a suture aperture defined therethrough, the suture aperture configured to receive a looped suture or other looped material. The distal end portion also includes a slot configured to secure at least a distal portion of the implantable sheet therein.

In some embodiments, the slot of the delivery tool separates the distal end portion of the delivery tool into an upper and lower jaw member, the slot configured to secure a distal end portion of the implantable sheet between the upper and lower jaw members.

In embodiments, the delivery tool insert is configured to be received within the lumen of the delivery tool. The delivery tool insert includes a proximal end portion, a distal end portion, and at least one resilient arm extending therebetween, the at least one resilient arm configured to extend through the at least one window of the delivery tool.

In some embodiments, the distal end portion of the delivery tool insert further comprises at least one locking member extending therefrom and the distal end portion of the delivery tool further comprises at least one locking recess defined therethrough, the locking member configured to be secured in the at least one locking recess when aligned therewith, to lock the delivery tool insert within the lumen of the delivery tool.

In some embodiments, the central tie connects the mesh to the delivery tool, wherein the central tie passes through one or more tie holes defined through a central portion of the elongate body of the delivery tool forming a loop inside the lumen of the delivery tool and extending away from the delivery tool through the second face of the mesh and forming a handle extending away from the opposite first face of the mesh.

In embodiments, the rolling device includes a tubular body defining a channel therein. The tubular body also includes a first slit which extends along a length of the tubular body and is in communication with the channel. A tie handle opening is defined within a portion of the tubular body and is configured to receive a tie handle of a central tie therein. The channel may be circular or conical. The rolling device may further include a spout, a flange, and/or a fin.

In embodiments, a two-piece implantable sheet delivery device is described including a delivery tool including an elongate body extending between a proximal end portion and a distal end portion, the elongate body including a lumen extending therethrough and a pair of windows defined in a sidewall of the elongate body, the pair of windows configured to allow access to the lumen from outside of the elongate body, and, a delivery tool insert configured to be received within the lumen of the elongate body, the delivery tool insert including a proximal end portion, a distal end portion, and a pair of resilient arms extending therebetween, the pair of resilient arms configured to extend through the pair of windows when aligned therewith, wherein the two-piece delivery device is configured to transition between a restrained configuration and an expanded configuration.

Methods of repairing a soft tissue defect, and particularly a hernia such as a ventral hernia are also described. In some embodiments, the methods include forming a rolled sheet-tool assembly, inserting a delivery tool insert into a lumen of the delivery tool of the rolled sheet-tool assembly to form a rolled sheet-tool-insert assembly, inserting the rolled sheet-tool-insert assembly into a patient via a trocar, deploying the sheet inside the patient, positioning and fixating the sheet inside the patient, and withdrawing the delivery tool including the delivery tool insert from the patient.

In some embodiments, the delivery tool insert is in a narrowed or restrained configuration in the rolled sheet-tool-insert assembly. In some embodiments, the delivery tool insert transitions to an expanded configuration when deployed.

In some embodiments, the methods include, combining an implantable sheet, a central tie, and a delivery tool to form a sheet-tool assembly, the delivery tool including an elongate body extending between a proximal end portion and a distal end portion, the elongate body including a lumen extending therethrough and at least one window defined in a sidewall of the elongate body, the window configured to allow access to the lumen from a side of the elongate body, preparing the sheet-tool assembly for insertion into a patient by using a rolling device to form a rolled sheet-tool assembly, inserting a delivery tool insert into the lumen of the delivery tool of the rolled sheet-tool assembly to form a rolled sheet-tool-insert assembly, the delivery tool insert including a proximal end portion, a distal end portion, and at least one resilient arm extending therebetween, the at least one resilient arm configured to extend through the at least one window when aligned therewith, inserting the rolled sheet-tool-insert assembly into a patient via a trocar using the rolling device, deploying the sheet inside the patient, positioning and fixating the sheet inside the patient, and withdrawing the delivery tool including the delivery tool insert from the patient.

BRIEF DESCRIPTION OF THE DRAWINGS

Various embodiments of the kits and/or components are described herein with reference to the drawings wherein:

FIG. 2A is a perspective view of a delivery tool described in at least one embodiment herein;

FIG. 2B is a side view of a delivery tool described in at least one embodiment herein;

FIGS. 13A-13G are cross-sectional schematic views of a method of using the kits and/or components described herein in treating a soft tissue defect as described in at least one embodiment herein.

DETAILED DESCRIPTION

The present disclosure describes a kit suitable for repairing various soft tissue defects, and particularly for repairing various types of hernias. The kit can include any of the following components, individually or in any combination: An implantable sheet, a central tie, a flexible delivery tool, a delivery tool insert, a rolling device, and an insertion member. The delivery tool and the delivery tool insert are configured to be combined to form a two-piece delivery device.

In some embodiments, the kits described herein may include at least an implantable sheet, a central tie, a flexible delivery tool configured to be secured to a portion of the implantable sheet, and a delivery tool insert. Such kits may further include a rolling device, an insertion member, or both.

In some embodiments, the kits include an implantable sheet, a flexible delivery tool including a central tie extending therefrom, a delivery tool insert, a rolling device, and an insertion member.

In some embodiments, the kits described herein may include at least an implantable mesh, a central tie, a flexible delivery tool configured to be secured to a portion of the implantable mesh, and a delivery tool insert. Such kits may further include a rolling device, an insertion member, or both.

In some embodiments, the kits include an implantable mesh, a flexible delivery tool including a central tie extending therefrom, a delivery tool insert, a rolling device, and an insertion member.

The present disclosure further describes packaging for any of the kits and/or the individual components of the kits described herein. As well as methods of treating or repairing various soft tissue defects or hernias utilizing any of the kits and/or components described herein. Methods of preparing, inserting, orienting, deploying, and/or fixating of an implantable sheet using the various components descried herein are also provided.

Figure 1:
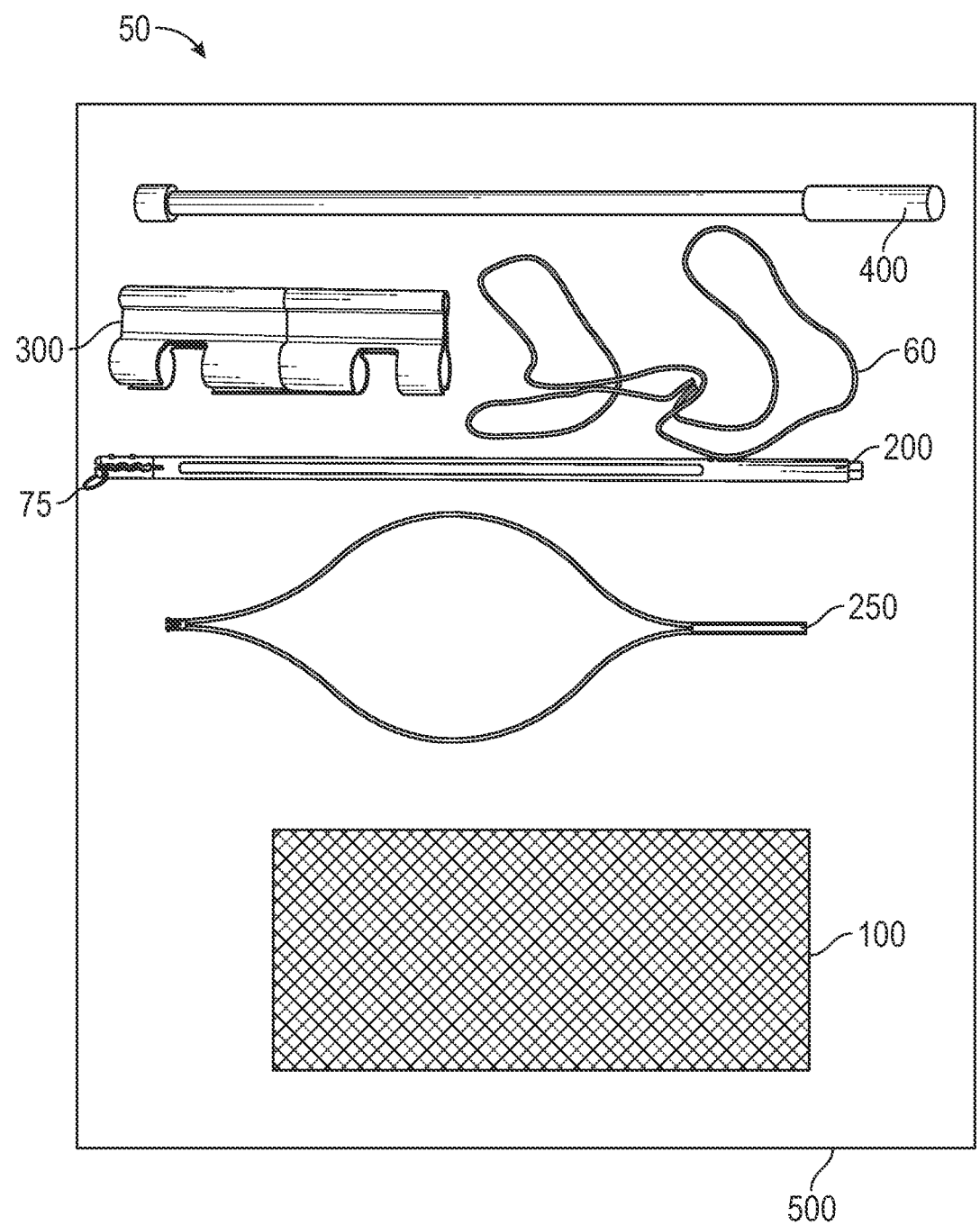
FIG. 1 is top view of a kit described in at least one embodiment herein.

In FIG. 1, a kit 50 as described in at least one embodiment herein is depicted. The kit 50 includes at least an implantable sheet 100, a delivery tool 200 and a delivery tool insert 250. The kit 50 is shown being positioned or stored in a package 500 and further including a rolling device 300, an insertion member 400, and a central tie 60 and a looped material or suture 75 extending from delivery tool 200. Each of these components are provided in more detail hereinbelow.

I. Implantable Sheet

By implantable, the sheets described herein are configured to be positioned at a location within a body for any sufficient amount of time to at least temporarily treat and/or repair a soft tissue defect. In some embodiments, the biocompatible sheet is configured to be located within a portion of the abdominal cavity.

The implantable sheets described herein can be generally planar and may include any biocompatible porous or non-porous material configured to treat and/or repair a soft tissue defect. Some non-limiting examples of suitable sheets include surgical mesh, tissue scaffolds, adhesion barriers, surgical slings, surgical foams, and combinations thereof. The implantable sheet may be woven, non-woven, knitted, braided, cast, extruded, pressed, lyophilized, and the like. The implantable sheet can be bioresorbable, partially bioresorbable or non-bioresorbable.

In some embodiments, the implantable sheets described herein are surgical mesh. In the context of this application the term "mesh", "surgical mesh", or "implantable mesh" refers to an arrangement of biocompatible filaments or yarns, for example a knitted material or woven or nonwoven fibrous material, arranged in a manner to include pores within the mesh face that can encourage tissue ingrowth. The mesh can be bioresorbable, partially bioresorbable or non-bioresorbable. The mesh is generally planar or includes at least a portion which is generally planar. The mesh includes first and second opposite faces and an outer perimeter which defines a center of the mesh on each face. The mesh is also flexible enough to be rolled onto the exterior of the delivery tool and upon itself prior to insertion into a patient or a cavity defined within of a patient. The mesh can be produced from one or more layers of fabric and may optionally include an anti-adhesion barrier layer positioned on at least one portion or one side of the fabric thereby forming a composite mesh. Such meshes are well known to the person skilled in the art. The mesh can also be provided in any shape (rectangular, square, circular, oval, etc.) and size. In some embodiments, the mesh may be round or elliptical in shape when unrolled.

The implantable mesh may be a two-dimensional knitted fabric or a three-dimensional knitted fabric. In the context of the present application, the expression "two-dimensional knitted fabric" means a knitted fabric having two opposite faces linked together by stitches but having no spacers imparting a certain thickness to it: such a knitted fabric may be obtained, for example, by knitting threads on a warp or Raschel knitting machine using two guide bars. Examples of two-dimensional knitted fabrics suitable for the present invention are given in the document WO2009/071998.

In the present application, the expression "three-dimensional knitted fabric" means a knitted fabric having two opposite faces linked together by spacers imparting a significant thickness to the knitted fabric, said spacers consisting of connecting threads additional to the threads forming the two faces of the knitted fabric. Such a knitted fabric may be obtained, for example, using a double-bed Raschel knitting machine or warp knitting machine with a plurality of guide bars. Examples of knitting three-dimensional knitted fabrics suitable for the present invention are given in the documents WO99/05990, WO2009/031035, WO2009/071998.

Additionally, meshes within the scope and context of this disclosure may include fibrous biologic materials such as allografts (i.e., AlloDerm® Regenerative Tissue Matrix from Allergan), autografts, and xenografts (i.e., PERMACOL™, from Medtronic).

In some embodiments, the implantable sheets described herein are configured for use in minimally invasive surgical procedures. In some embodiments, the implantable sheets described herein are configured for use with surgical techniques including, but not limited to, TAPPS (transabdominal preperitoneal surgery), TEPS (totally extraperitoneal surgery) or IPOM (intra peritoneal onlay mesh) techniques.

In particularly useful embodiments, the implantable sheet is a surgical mesh or composite surgical mesh suitable for repairing a ventral hernia. In particularly useful embodiments, the implantable sheet is a surgical mesh or composite surgical mesh suitable for repairing a ventral hernia using any appropriate surgical technique, including but not limited to TAPPS, TEPS, or IPOM techniques.

II. Central Tie

The central tie is designed to connect and/or secure a portion of the two-piece delivery device, and particularly a central portion of the delivery device, to the implantable sheet, and particularly a central portion of the implantable sheet, without interfering the movement of the one or more resilient arms (of the delivery tool insert) through the one or more windows (of the delivery tool).

In some embodiments, the central tie is designed to form at least one loop within the lumen of the delivery tool and at least one tie handle extending away from the delivery tool. The at least one tie handle passing through the first and second opposite faces of the implantable sheet and away from the implantable sheet. The at least one tie handle is configured to have a length sufficient to be manipulated from outside the body during implantation. In some embodiments, the central tie is positioned on or near a center of both faces of the implantable sheet.

The central tie can made of any absorbable or nonabsorbable material and has a length greater than its width. For example, the central tie can be in the form of a suture, a fiber, a cable, a chord, a chain, a strip, a ribbon, a tether, a strap, or a long thin tubular mesh.

In some embodiments, the central tie is formed from one suture passing through the delivery tool and both sides of the sheet to form the tie loop and the tie handle. In some embodiments, the central tie is formed from two or more sutures wherein at least a first suture forms the tie loop and the second suture forms the tie handle. The suture can be bioresorbable, partially bioresorbable or non-bioresorbable. The suture can be barbed or non-barbed. The suture can be armed or unarmed on the ends of the suture handle.

In some embodiments, the tie loop can be preformed in the central tie. In some embodiments, the central tie is woven or laced around itself to form the tie loop.

In embodiments wherein the sheet includes an anti-adhesion barrier on at least a central portion thereof, the central tie may also pass through the barrier.

On the second opposite top face, the central tie extends from the sheet a length sufficient to form a tie handle configured to be passed from the inside of the patient to the outside of the patient. In some embodiments, the tie handle is simply formed by the end(s) of the one or more ties extending from the second opposite face. In some embodiments, the central tie forms two handles extending from the second top face of the implantable sheet.

The tie handle is also designed to assist with preparing the sheet for rolling in rolling device, as well as making it simpler to center the sheet on the defect prior to deployment.

In some embodiments, the central tie is added to the delivery tool prior to packaging and/or during the manufacturing process of the delivery tool. In some embodiments, the central tie may be stored separately in the kit or package and can be added to the delivery tool by the surgeon after the package is open. In still other embodiments, the central tie may be a suture packaged separately from the delivery tool and added to the delivery tool by the surgeon immediately prior to implantation.

In some embodiments, the implantable sheet is an implantable mesh and the central tie is a suture.

III. Delivery Tool

The kits described herein include a two-piece delivery device including a delivery tool as the first piece and a delivery tool insert as the second piece. The delivery tool will now be described.

The kits described herein can include a delivery tool alone or in combination with at least the implantable sheet, the delivery tool insert, and the central tie. Some other kits include a delivery tool alone or in any combination of the components described herein.

The delivery tool includes a flexible rod having an elongate body configured to adapt to the curvature of a cavity inside a patient's body, such as an insufflated abdominal cavity. By being flexible, the delivery tool will not cause damage to tissue or organs inside the patient in the event the tool comes into direct contact with tissues or organs located inside the patient's cavity, such as the abdominal wall or organs inside an abdominal cavity. In addition, the flexible nature of the delivery tool makes it easier for the tool to enter the distal end of a trocar located inside the cavity during the withdrawal or removal process of the surgical procedure. Although flexible, the delivery tool still maintains a rigidity sufficient to generally support an implantable sheet on an outer surface thereof and in a rolled configuration thereon.

In some embodiments, the flexible delivery tool, in its natural state, is a straight or unbent rod with the proximal and distal end portions generally 180 degrees apart. In such embodiments, the flexible delivery tool may further include the ability to bend to a curvature of at least 120 degrees when stressed, while maintaining the ability to return to its naturally straight or unbent configuration upon removal of stress. In some embodiments, the flexible delivery tool may further include the ability to bend to a curvature of at least 90 degrees when stressed, while maintaining the ability to return to its naturally straight or unbent configuration upon removal of the stress.

The delivery tool can be made of any biocompatible material displaying the appropriate flexibility characteristics. Some non-limiting examples of suitable materials include polyamides, polyaryl ether ketone (PAEK), acrylonitrile butadiene styrene (ABS), polyether ether ketone (PEEK), polyoxymethylene (POM), nitinol (NiTi), polyetherimide (PEI), polycarbonates (PC), and combinations thereof. In addition to being biocompatible the materials used to form the delivery tool can be compatible with injection molding manufacturing processes and compatible with standard sterilization methods, such as Ethylene Oxide and gamma radiation.

As shown in more detail in FIGS. 2A and 2B, the delivery tool 200 described herein includes a flexible rod including an elongate body 205 extending along longitudinal axis $A_1$ between a proximal end portion 210 and a distal end portion 220 with a central portion 215 positioned therebetween. The elongate body 205 includes a lumen 206 extending therethrough and at least one window 207 defined in a sidewall 205a of the elongate body 205. The lumen 206 extends at least partially, and in some embodiments completely, through the elongate body 205 from the proximal end 210a towards distal end 220a. The lumen 206 is configured to receive the delivery tool insert (not shown in FIGS. 2A-2B). The window 207 is an opening in sidewall 205a configured to allow access to the lumen 206 from a side of the elongate body 205. The window 207 is also configured to allow a resilient arm of the delivery tool insert (not shown in FIGS. 2A-2B) to pass therethrough and extend outwardly from the delivery tool, when the resilient arm is aligned therewith.

In some embodiments, at least a part of the proximal end portion 210 is shaped or contoured differently than the central portion 215 of the elongate body 205. For example, as shown in FIGS. 2A and 2B, the shaped proximal end portion 210 may be thinner, i.e., has a smaller outer perimeter, than the central portion 215 of the elongate body. Alternatively, in some embodiments, the shaped proximal end portion may be thicker, i.e., has a larger outer perimeter, than the elongate body. In either instance, the shaped proximal end portion 210 of the delivery tool 200 can include any suitable shape or contour. As provided specifically in FIGS. 2A-2B, in some embodiments, the proximal end portion 210 may include a hexagonal design, as compared to the central portion 215 of the elongate body 205 having a round design. Other various combinations of shapes of the proximal end portion and the central portion of the elongate body are also envisioned including, but not limited to, triangular shaped, pentagonal shaped, heptagonal shaped, octagonal shaped, star-shaped, cross-shaped, and combination thereof.

The proximal end portion 210 is configured to connect to a distal end portion of an insertion member (not shown in FIGS. 2A-2B). The shaped proximal end portion 210 is also configured to be used to roll or rotate the implantable sheet around the elongate body 205 of the tool 200 when a portion of the sheet is secured to the distal end portion 220 of the tool 200. Once the implantable sheet is rolled around the tool 200, the proximal end portion 210, alone or in combination with the insertion member, can also be used to manipulate the tool 200 in a distal direction through a trocar and into the patient or the abdominal cavity specifically.

As further provided in FIGS. 2A-2B, the delivery tools 200 described herein also include a distal end portion 220 including a slot 230 extending longitudinally from the distal end 220a of the elongate body 205 towards the central portion 215 of the elongate body 205. The slot 230 divides the distal end portion 220 into an upper jaw member 231 and a lower jaw member 232. The slot 230 is configured to receive and secure at least a portion of an implantable sheet between the upper and lower jaw members 231, 232. In some embodiments, the slot 230 is configured to receive and secure a distal end portion of a sheet which can be folded over one of the upper or lower jaw members 231, 232, as well as the distal end 220a of the delivery tool 200.

In some embodiments, the slot 230 extends generally along a central longitudinal axis $A_1$ of the elongate body thereby dividing the distal end portion 220 into symmetrical upper and lower jaw members 231, 232. However, it is envisioned that in some embodiments, the slot may be offset from the central longitudinal axis dividing the distal end portion into asymmetrical upper and lower jaw members.

As shown, the slot 230 defines a wavy or sinusoidal pathway through the distal end portion 220 of the delivery tool 200. In some embodiments, the slot may be generally linear as compared to wavy or sinusoidal. The wavy or sinusoidal pathway provides a greater surface area to the slot 230 thereby increasing the surface area in contact with the implantable sheet when positioned in the slot 230. This increased surface area improves the hold strength of the slot 230 on the sheet, as compared to a slot having a generally linear pathway. The number and/or size of the waves can vary to optimize the hold strength of the delivery tool.

In addition to being configured to receive and retain a portion of the implantable sheet within the slot 230 defined in the distal end portion 220 of the delivery tool 200, the upper and lower jaw members 231, 232 are also flexible. The upper and lower jaw members 231, 232 are made of the same flexible material which forms the elongate body 205. Therefore, the jaw members 231, 32 possess a naturally flexibility that can be used to either expand the size of the slot 230 by forcing the jaw members 231, 232 away from each other to remove the implantable sheet from the slot or decrease the size of the slot 230 by forcing the jaw members 231, 232 towards each other thereby pinching the jaw members 231, 232 onto the sheet positioned therebetween.

As described in more detail hereinbelow, prior to insertion or implantation, the implantable sheet is rolled around the delivery tool, and specifically the distal end portion of the delivery tool, while positioned within a rolling device. When the rolling occurs within the rolling device, pressure is applied to the upper and lower jaw members to pinch together or get closer narrowing the slot with the implantable sheet positioned therein. This self-clamping effect is maintained while the implantable sheet and delivery tool are maintained in the rolling device, as well as through the trocar during insertion. When removed from the rolling device or trocar, such as when the implantable sheet and delivery tool are inserted into a patient's body, the additional pressure is removed and the self-clamping effect is diminished allowing the upper and lower jaw members to start to return back to their natural spaced-apart position making it easier to release the distal end of an implantable sheet.

To further enhance the self-clamping effect, the distal end portion of the delivery tool may further include some at least one crenulation 209 extending outwardly from an outer surface of at least one of the upper or lower jaw members 231, 232. Unlike waves or teeth which extend into the slot 230 defined between the upper and lower jaw members 231, 232, crenulations 209 extend outwardly from at least one of the jaw members 231, 232. The crenulations 209 are configured to engage the implantable sheet, and particularly the open pores of the implantable sheet, during rolling to improve the ability of the delivery tool to tightly roll the sheet thereon. The crenulations 209 are shown as generally round and may include a point at a tip thereof. It is envisioned that the crenulations 209 can be of any shape useful for engaging the implantable sheet during rolling.

Although shown on only one of the jaw members, it is envisioned that the crenulations may be on both jaw members and/or may be positioned on an outer surface of at least a portion of the elongate body of the delivery tool.

The distal end portion 220 may also include at least one suture aperture 222 configured to receive a looped material or suture 75 therethrough (see FIG. 1 for looped material or suture). The suture aperture 222 may be positioned on the most distal portion of the delivery tool to make it easily accessible when inside the patient because the suture aperture 222 leads the way when the delivery tool is withdrawn from the patient. The looped suture or material positioned within and extending from the suture aperture 222 also provides a larger target to grasp when retrieving the delivery device and/or the delivery tool, as compared to the distal end of the delivery tool without a looped suture or material. In some embodiments, the suture aperture 222 is positioned proximal to the slot 230. In some embodiments, the suture aperture 222 is positioned on a distal end portion of either of the upper or lower jaw members 231, 232. In some embodiments, the suture aperture 222 is positioned on a proximal end portion 210 of the delivery tool 200.

As further depicted in FIGS. 2A-2B, in some embodiments, the shape and/or thickness of the central portion 215 and the distal end portion 220 of the delivery tool 200 is generally the same, not including the crenulations 209.

In addition to the proximal and distal end portions 210, 220, the elongate body 205 includes a central portion 215 including a lumen 206 defined therein and one or more tie holes 202 defined through the sidewall 205a. The lumen 206 extends from the proximal end 210a through the central portion 215 towards the distal end portion 220 of the elongate body 205. In some embodiments, as shown in FIGS. 2A-2B, the lumen 206 extends from the shaped proximal end 210a through the central portion 215 and ends proximal to the slot 230 defined in the distal end portion 220. The one or more tie holes 202 are configured to allow the central tie described herein to pass therethrough. In some embodiments, a pair of tie holes 202 allow the central tie to enter the elongate body 205 by passing through the sidewall 205a via one of the two tie holes 202 and extending a length inside the lumen 206 before exiting the lumen 206 by passing through the sidewall 205a via the other of the two tie holes 202.

The central portion 215 of the elongate body 205 further includes at least one window 207. As can be seen best in FIG. 2B, in some embodiments, the elongate body 205 of the delivery tool 200 may include a pair of windows 207 aligned relative to each other on opposite sides of the elongate body 205. Thus, as shown in FIG. 2B, from a side view, the windows 207 overlap and render a portion of the central portion 215 see-through.

The elongate body 205 also includes at least one locking recess 204. The locking recess 204 is defined in a portion of sidewall 205a. In some embodiments, the locking recess 204 extends completely through sidewall 205a. The locking recess 204 is configured to receive a locking tab provided on the delivery tool insert (not shown in FIG. 2A-2B) to secure and/or lock the delivery tool insert inside the lumen 206 of the delivery tool 200. In FIGS. 2A-2B, the two or more locking recesses are shown aligned relative to each other on opposite sides of the elongate body 205 distal to the one or more windows 207 and proximal to the slot 230. However, the one or more locking recesses can be located on various different portions of the elongate body.

In some embodiments, the implantable sheet is an implantable mesh and the flexible delivery tool is a mesh delivery tool.

In some embodiments, the implantable sheet is an implantable mesh, the central tie is a suture, and the flexible delivery tool is a mesh delivery tool.

IV. Delivery Tool Insert

As previously noted, the kits described herein include a two-piece delivery device including a delivery tool as the first piece and a delivery tool insert as the second piece. The delivery tool insert will now be described.

The kits described herein can include a delivery tool insert alone or in combination with the delivery tool, the implantable sheet and the central tie. Some other kits include a delivery tool insert alone or in any combination of the components described herein.

The delivery tool insert is configured to be received and secured within the lumen of the elongate body of the delivery tool. The delivery tool insert includes a shaped proximal end portion, a distal end portion, and at least one resilient arm extending therebetween.

The delivery tool insert can be made from any biocompatible material displaying the appropriate flexibility characteristics. Some non-limiting examples of suitable materials include polyethylene, polypropylene, polyamides, polyaryl ether ketone (PAEK), acrylonitrile butadiene styrene (ABS), polyether ether ketone (PEEK), polyoxymethylene (POM), nitinol (NiTi), polyetherimide (PEI), polycarbonates (PC), and combinations thereof. In some embodiments, at least the resilient arms of the delivery tool insert can be made from polyamides, polyether ether ketone (PEEK), and nitinol (NiTi).

In addition to being biocompatible the materials used to form the delivery tool insert can be compatible with injection molding manufacturing processes and compatible with standard sterilization methods, such as Ethylene Oxide and gamma radiation.

As shown in more detail in FIGS. 3A-3E, the delivery tool insert 250 described herein includes a proximal end portion 260, a distal end portion 270 and one or more resilient arms 265a. In some embodiments, the insert 250 includes a pair of resilient arms 265a, 265b.

The proximal end portion 260 and the distal end portion 270 of the delivery tool insert 250 define a longitudinal axis $A_3$ with the one or more resilient arms 265a connecting the proximal end portion 260 to the distal end portion 270. As depicted, the one or more resilient arms 265a, 265b do not extend along the longitudinal axis $A_3$ of the delivery tool insert 250. Rather, the one or more resilient arms 265a, 265b display a natural bias to extend away from the longitudinal axis $A_3$ (see arrows in FIG. 3A). As shown, in some embodiments, the delivery tool insert 250 includes a pair of resilient arms 265a, 265b which naturally form a generally circular or eye shaped opening 267 therebetween. In some embodiments, the pair of resilient arms 265a, 265b are spaced apart from each other continuously between the proximal and distal end portions 260, 270 creating a proximal gap 267a and a distal gap 267b. The proximal gap 267a being the most proximal portion of the opening 267 and the distal gap 267b being the most distal portion of the opening 267. It is envisioned that the resilient arms can be configured to form a variety of differently shaped openings including, but not limited to, square, triangular, octagonal, hexagonal, elliptical, and the like.

Figure 3A:
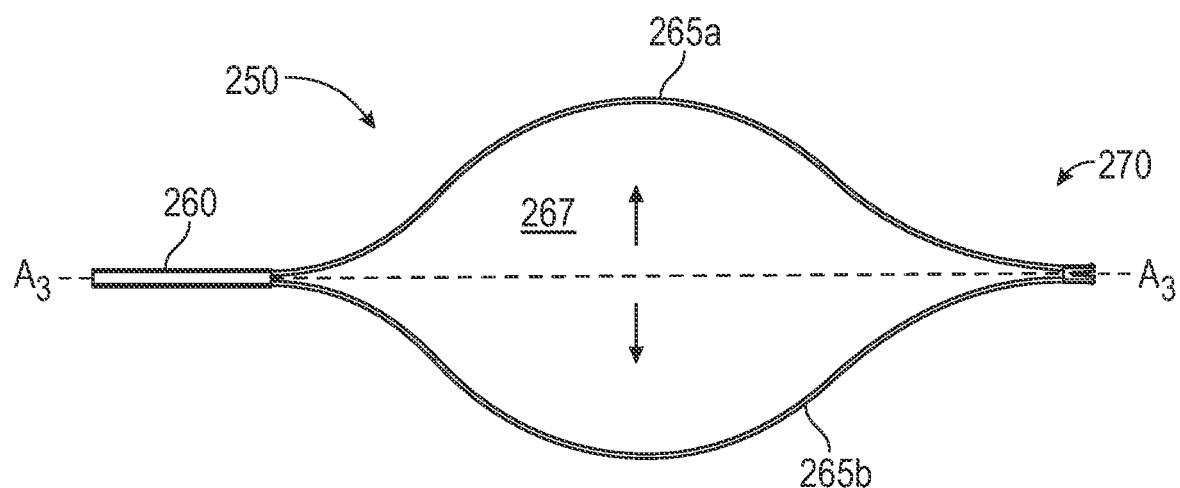
FIG. 3A is a top view of a delivery tool insert described in at least one embodiment herein.
Figure 3B:
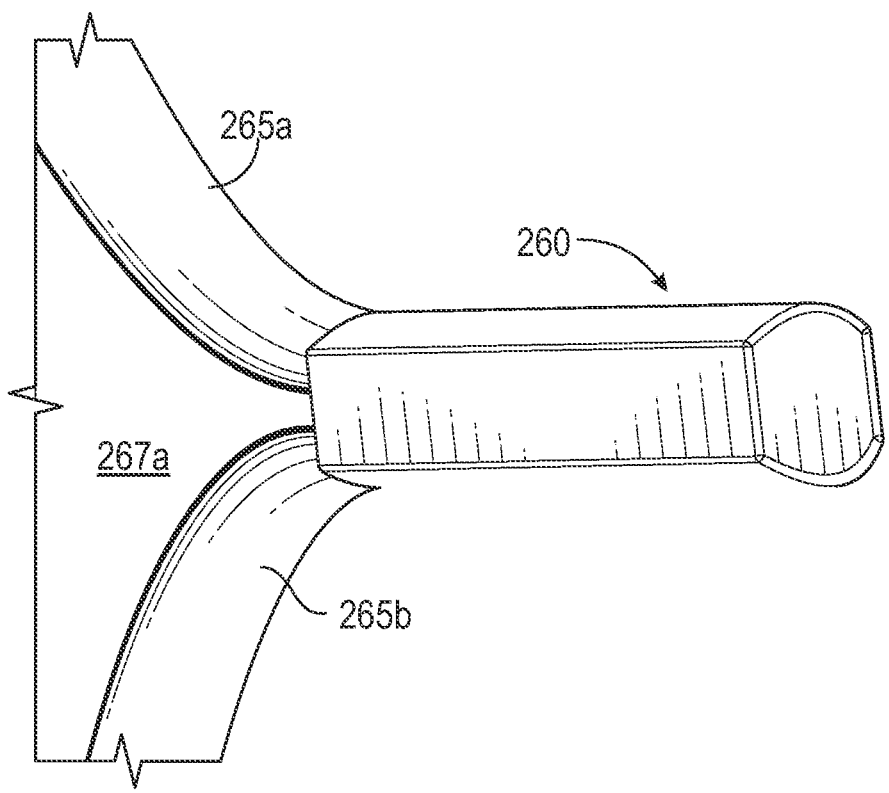
FIGS. 3B and 3C are perspective views of a proximal and distal end portion of the delivery tool insert of FIG. 3A and described in at least one embodiment herein.
Figure 3C:
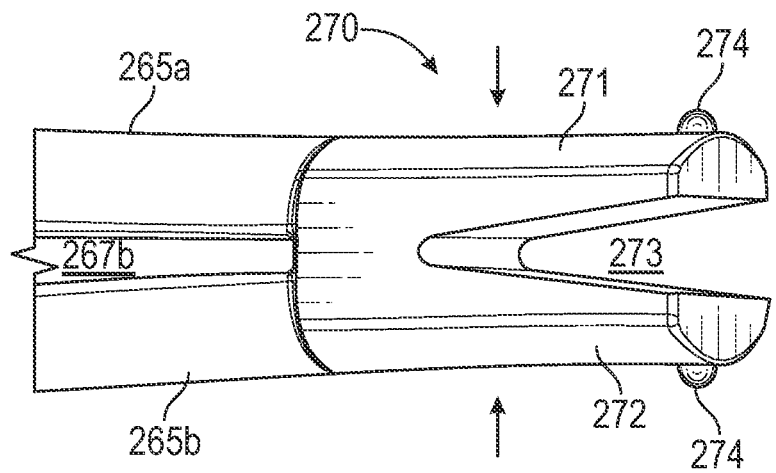
Figure 3D:
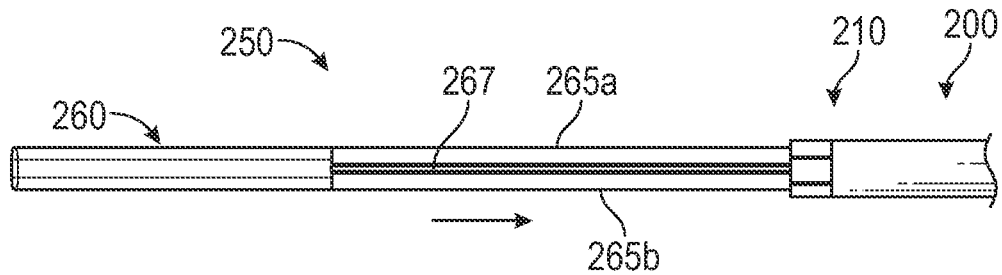
FIG. 3D is a side view of the delivery tool insert of FIG. 3A in combination with a delivery tool of FIG. 2B to form a two-piece delivery device as described in at least one embodiment herein.
Figure 3E:
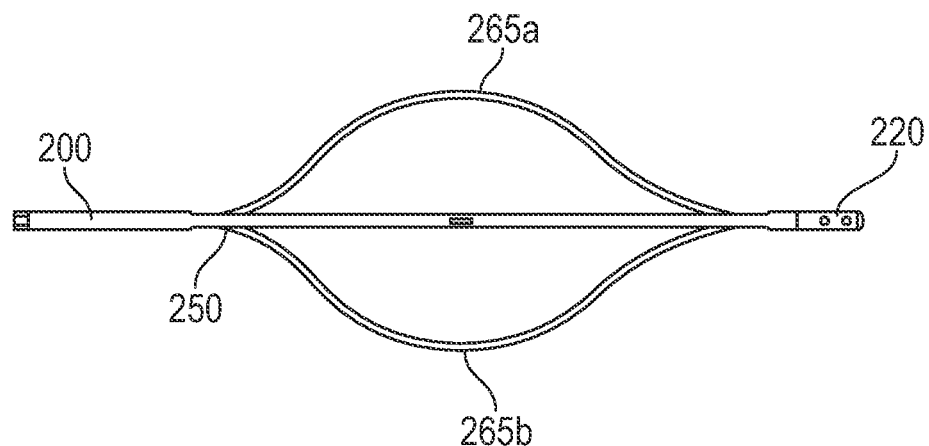
FIG. 3E is a top view of a two-piece delivery device in an expanded configuration as described in at least one embodiment herein.

The one or more resilient arms are configured to transition between an expanded configuration and a narrowed or restrained configuration (FIG. 3D). The one or more resilient arms are naturally configured in an expanded configuration wherein the one or more resilient arms automatically move and/or are located away from the longitudinal axis $A_3$ and/or each other, as depicted in FIGS. 1, 3A, and 3E. The one or more resilient arms are not stressed in the expanded configuration. Also, the opening is largest in the expanded configuration and the overall length of the insert is shortest in the expanded configuration.

The one or more resilient arms can be stressed into a narrowed configuration wherein the one or more resilient arms are forced towards the longitudinal axis $A_3$ and/or each other, as depicted in FIG. 3D. In some embodiments, the proximal end portion of the delivery tool temporarily forces the one or more resilient arms into a narrowed or restrained configuration (FIG. 3D) during insertion of the delivery tool insert into the lumen of the delivery tool. However, the one or more resilient arms naturally return to the expanded configuration (FIG. 3E) by expanding through the one or more windows defined in the delivery tool. The opening is smallest in the narrowed configuration and the overall length of the insert is longest in the narrowed configuration.

At least a portion of the proximal end portion 260 and the distal end portion 270 of the delivery tool insert 250 is shaped or contoured. The shape or contour of the proximal end portion 260 and the distal end portion 270 are configured to fit within the shape or contour of the lumen 206 of the delivery tool 200. In some embodiments, the shape or contour of the proximal end 260 and/or the distal end portion 270 of the delivery tool insert 250 are generally the same as the shape or contour of the lumen 206 of the delivery tool 200.

In some embodiments, the shaped proximal and distal end portions 260, 270 of the delivery tool insert 250 are not simply cylindrical to help avoid rotation of the delivery tool insert 250 inside the delivery tool 200 to help maintain the one or more resilient arms 265a remain aligned with the one or more windows 207.

In some embodiments, as shown in FIG. 3C, a channel 273 is defined in the distal end portion 270 of the delivery tool insert 250. The channel 273 divides the distal end portion 270 into a first and second jaw member 271, 272. The channel 273 is configured to provide the distal end portion 270 the ability to flex inwardly and outwardly relative to the longitudinal axis $A_3$ when a force is applied inwardly (see arrows of FIG. 3C) and/or when the force is removed. This flexibility allows the distal end portion 270, and specifically the first and second jaw members 271, 272, to move inwardly slightly when slid into the lumen 206 of the delivery tool 200 (see FIG. 3D) while maintaining the ability to expand outwardly when the locking members 274 are aligned with locking recesses 204 defined in the sidewall of the delivery tool 200 thereby locking the distal end portion 270 of delivery tool insert 250 to the distal end portion 220 of the delivery tool 200. In some embodiments, the locking members 274 and the locking recesses 204 are generally round.

As can be seen in FIG. 3D, once the distal end portion 270 of the tool insert 250 is slid distally (see arrow of FIG. 3D)

into the lumen 206 of the delivery tool 200, the resilient arms 265a, 265b are forced to straighten or contract towards each other, shrinking opening 267, by the proximal end portion 210 of the delivery tool 200.

Figure 4A:
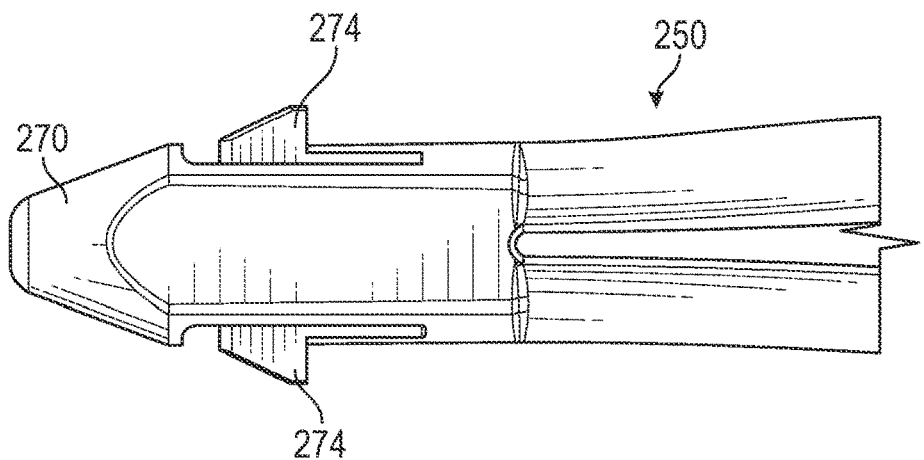
FIG. 4A is a top view of a distal end portion of the delivery tool insert described in at least one embodiment herein.
Figure 4B:
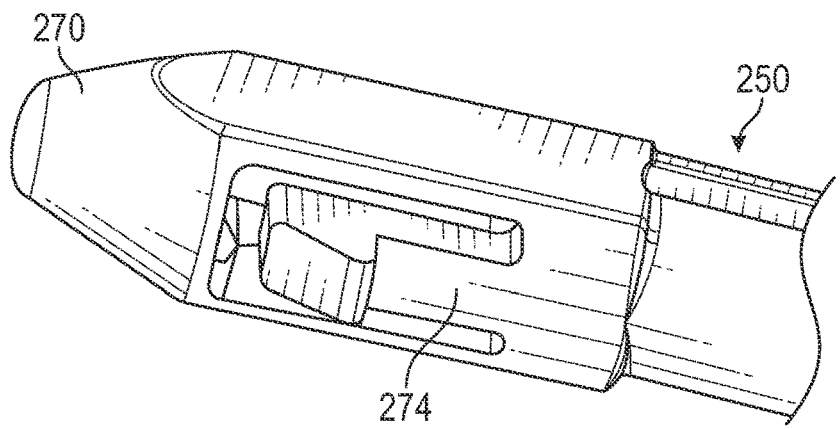
FIGS. 4B-4C are perspective views of the distal end portion of the delivery tool insert of FIG. 4A, alone and in combination with a delivery tool, described in at least one embodiment herein.
Figure 4C:
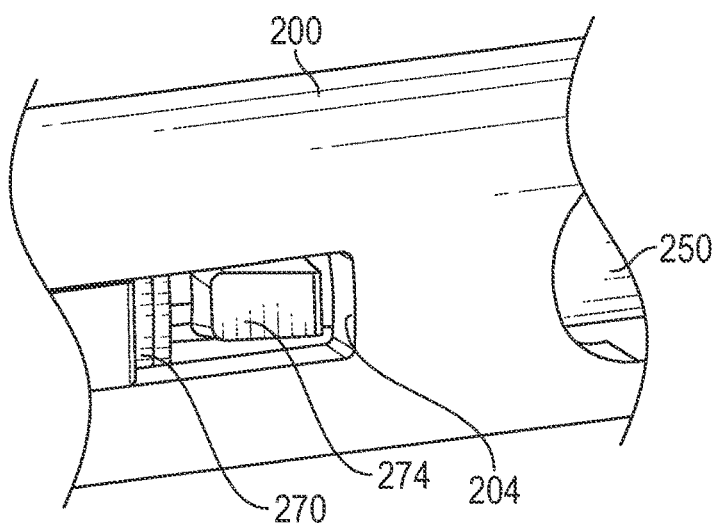

Turning to FIGS. 4A-4C, in some embodiments, the distal end portion 270 of the delivery tool insert 250 may be conically shape, like a headdress, rather than being divided by a channel. The conical shape end portion 270, unlike the channel 273, has a smoother outer surface configured to reduce friction or hanging during the passage through the delivery tool and the rolled implantable sheet. In addition, since the conical shaped end portion 270 is spaced distally from the locking members 274, shown as hooks, the conical shaped end portion 270 also protects the locking members from friction, hanging, or damage. The hooks or locking members 274 are shown locked with locking recess 204 in FIG. 4C. The hooks or locking members 274 can be forced or pressed inwardly towards each other to unlock the inner delivery tool insert 250 from the outer delivery tool 200.

V. Rolling Device

The rolling devices described herein are configured to prepare the implantable sheet and the delivery tool for insertion into a patient. The rolling device is used to wrap the implantable sheet around an outer surface of the flexible delivery tool to render the sheet in a rolled configuration prior to insertion of the delivery tool insert into the lumen of the delivery tool. The rolling device may also be used by a surgeon to transfer the delivery tool including the implantable sheet in a rolled configuration to a trocar for insertion into a patient. The rolling device, unlike the implantable sheet and delivery tool is not intended to be inserted into a patient.

Figure 5A:
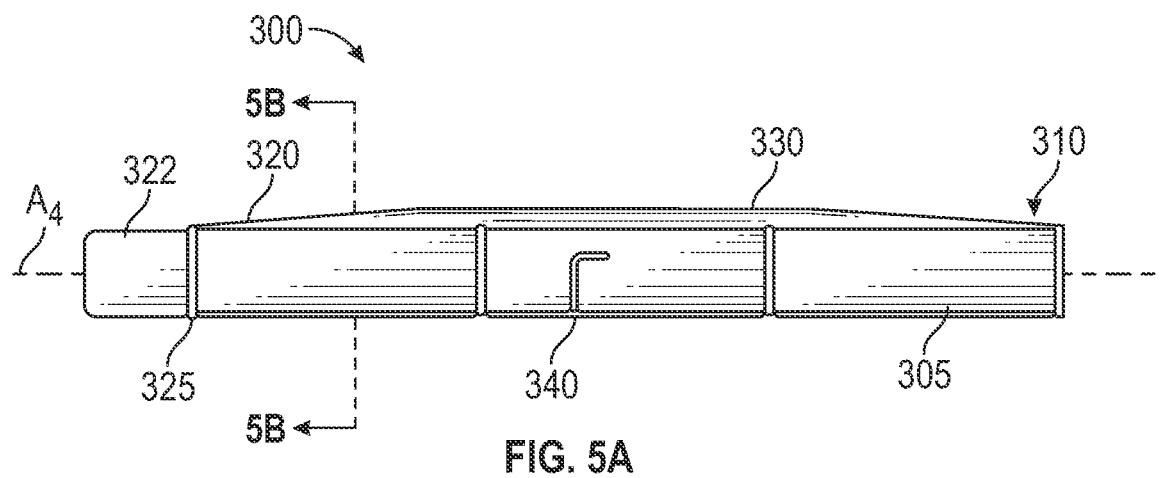
FIGS. 5A-5B include a side view and an end view, respectively, of a rolling device described in at least one embodiment herein.
Figure 5B:
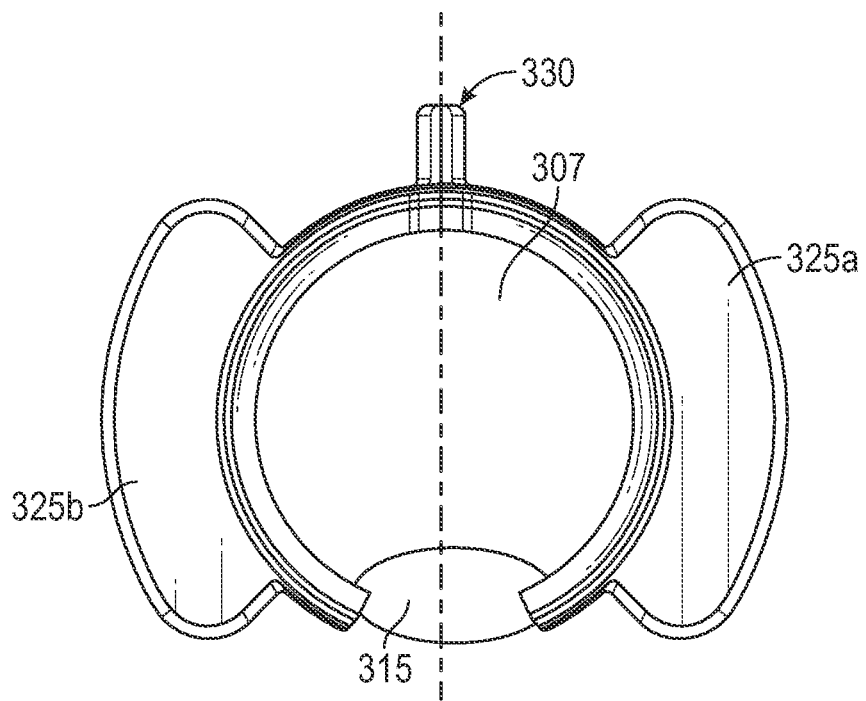

In FIGS. 5A-5B, a rolling device 300 is shown including a generally tubular body 305 extending between a proximal end portion 310 and a distal end portion 320 of the device 300, the tubular body 305 generally defines a channel 307 configured to receive the implantable sheet and the delivery tool. The channel 307 extends the entire length of the tubular body 305 through both the proximal and distal end portions 310, 320 of the device 300. A first slit 315 also extends the entire length of the tubular body creating an open generally tubular body 305 and/or an open channel 307. At least one fin 330 also extends along a length of the tubular body 305 and on an outer surface of the tubular body 305. The rolling devices described herein further include at least one tie handle opening 340 configured to receive the tie handle of the central tie prior to rolling. In some embodiments, the tubular body 305 may have a C-shaped cross-section.

The first slit 315 is configured to allow passage of the implantable sheet and the delivery tool into the channel 307 of the tubular body 305. The first slit 315 also provides the rolling device 300, which can be made of a rigid or semi-rigid material, the flexibility to expand or contract along the slit 315 as needed to accommodate different sizes of implantable sheet and delivery tools.

The rolling device 300 further includes a spout 322 and at least one flange 325 extending from the distal end portion 320. The spout 322 extends from the distal end portion 320 along the longitudinal axis $A_4$ of the device 300 and is configured to fit within or mate with a trocar opening to allow access into the trocar during insertion of the implantable sheet and delivery tool. The at least one flange 325 is positioned on the distal end portion 320 proximal to the spout 322 and extends generally perpendicular to longitudinal axis $A_4$ of the device 300. In some embodiments, the device 300 may include two flanges 325s, 325b, each positioned on opposite sides of the device 300. In some embodiments, the spout 322 can be designed as two separate half-circles, each positioned on opposite sides of the first slit 315.

As shown specifically in FIG. 5B, in some embodiments, the rolling device 300 includes a rigid fin 330 vertically aligned with, and in particular vertically centered on, the first slit 315. The device 300 may further include first and second flanges 325a, 325b positioned symmetrically on opposite sides of the fin 330. Also, the tie handle opening 340 may be defined within the outer wall of the tubular body 305 of the device 300 and may be generally L-shaped. Still further, as shown, the tubular body 305 can include a generally circular channel along the entire length of the device maintaining a generally constant diameter throughout.

Figure 6A:
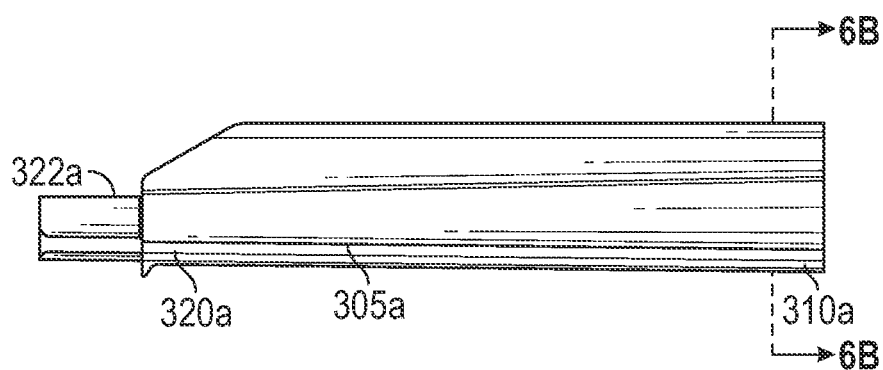
FIGS. 6A-6C include a side view, an end view, and a perspective view, respectively, of a rolling device described in at least one embodiment herein.
Figure 6B:
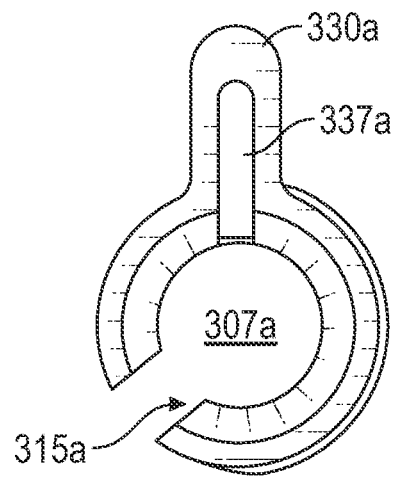
Figure 6C:
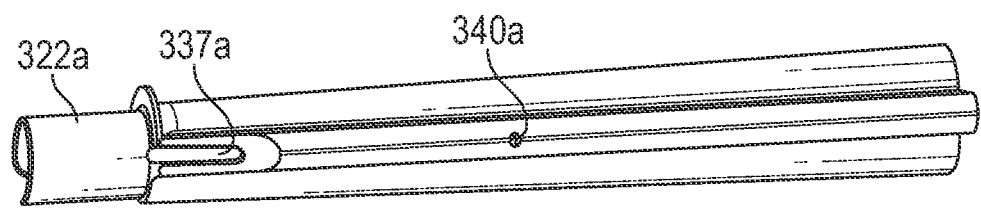

As shown in FIGS. 6A-6C, in some embodiments, the rolling device 300a includes a tubular body 305a having conical channel 307a, wherein the diameter of the channel 307a is widest at the proximal end portion 310a and narrows at the distal end portion 320a of the body 305a. The diameter of the tubular body 305a being narrowest near the spout 322a. The conical channel 307a has been shown to improve efficiency in rolling of the implantable sheet when the sheet is either elliptical in overall shape when laid flat or larger in length or width of about 20 centimeters.

In some embodiments, as further shown in FIGS. 6A-6C, the fin 330a defines a fin cavity 337a therein along at least a portion of the length of the fin 330a. The fin cavity 337a ends at the spout 322a. The fin 330a and/or the fin cavity 337a is not vertically aligned with the first slit 315a. The fin 330a and/or the fin cavity 337a is offset or at an obtuse angle to the first slit 315a. The fin 330a further includes a tie handle opening 340a depicted as a single hole located on and passing through a wall of the fin 330a, particularly at the peak of the fin 330a, which connects to the fin cavity 337a. The first hole 340a is configured to allow the tie handle of the central tie to pass vertically therethrough for loading of the implantable sheet and the delivery tool through the first slit 315a and into the channel 307a of the rolling device 300a. The fin cavity 337a is configured to allow the tie handle of the central tie to pass horizontally therethrough when the rolled implantable sheet and the delivery tool are moved or forced distally through the channel 307a to be inserted into the trocar.

Figure 7A:
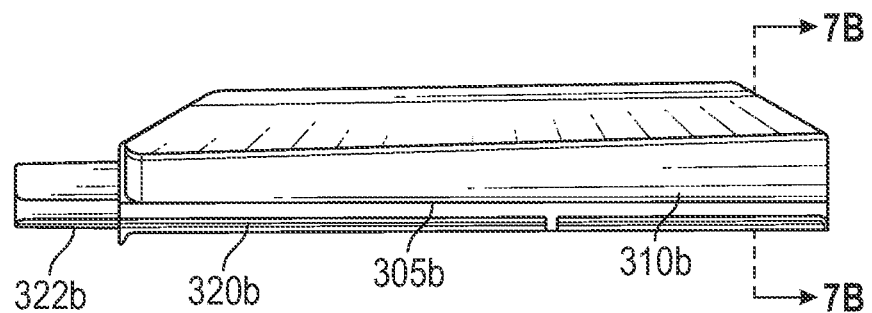
FIGS. 7A-7C include a side view, an end view, and a perspective view, respectively, of a rolling device described in at least one embodiment herein.
Figure 7B:
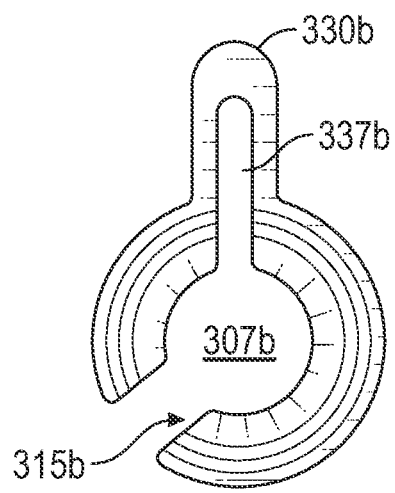
Figure 7C:
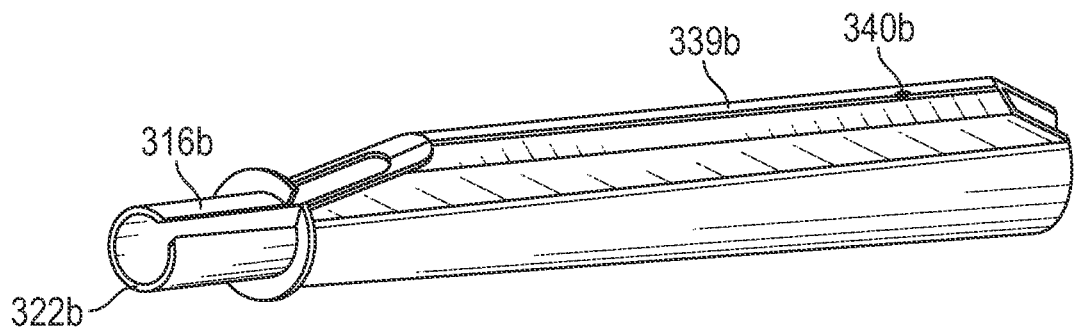

In some embodiments, as shown in FIG. 7A-7C, the fin cavity 337b does not end at the spout 322b but rather connects to a second slit 316b extending through the spout 322b. In addition, the fin cavity 337b extends through the peak of the fin 330b creating a fin groove 339b extending from the tie handle opening 340b distally towards the spout 322b. The fin cavity 337b, the fin groove 339b, and the second slit 316b of the spout 322b are all connected to allow the tie handle of the central tie to pass vertically and/or horizontally therethrough.

Figure 8B:
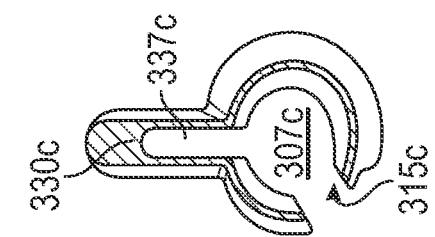
FIGS. 8A-8C include a side view, an end view, and a perspective view, respectively, of a rolling device described in at least one embodiment herein.
Figure 8A:
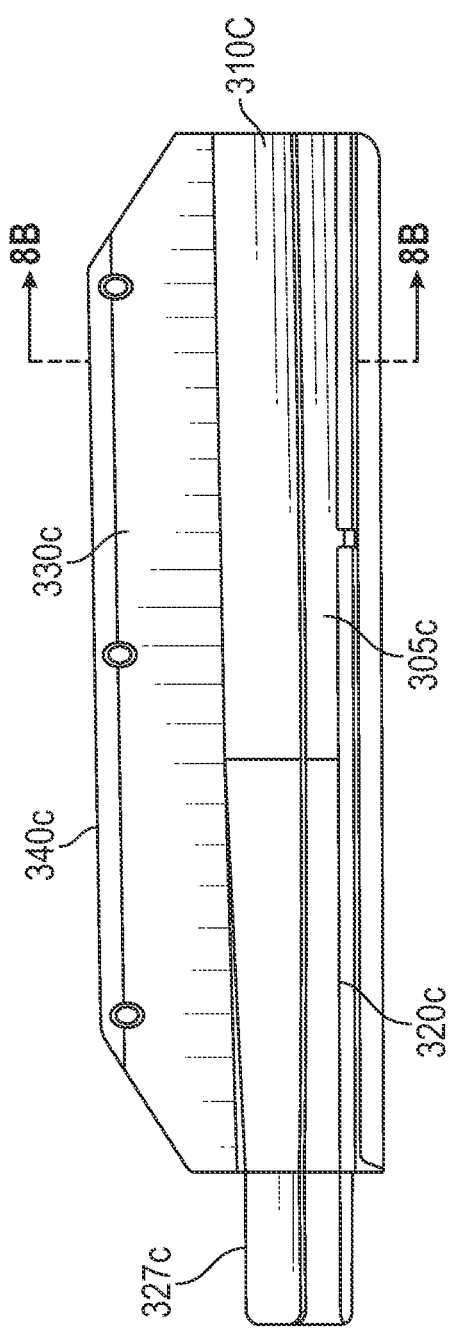
Figure 8C:
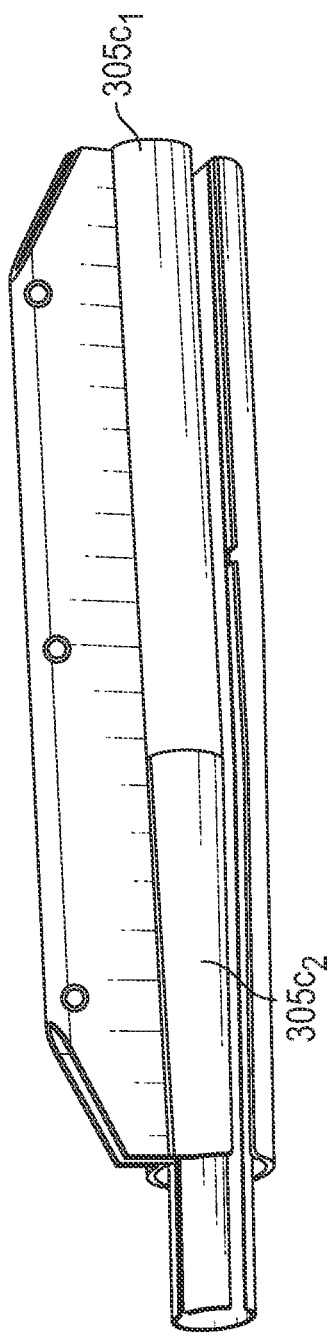

In FIGS. 8A-8C, in some embodiments, the tubular body 305c is both cylindrical in a first proximal part 305ci and conical in second distal part 305c2. The first proximal part 305ci includes a cylindrical shape wherein the diameter of the channel 307c remains constant and extends greater than or equal to 50% of the length of the elongate body 305c. The second distal part 305c2 includes the conical shape wherein the diameter of the channel changes, and particularly narrows. The conical part of the device extends 50% or less of the length of the elongate body 305c.

Figure 9:
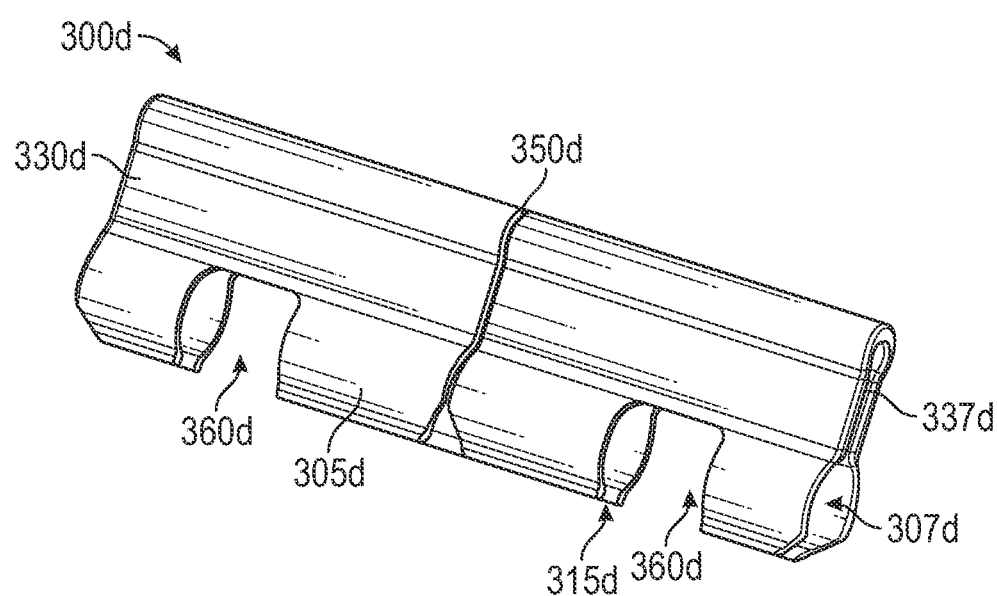
FIG. 9 is a perspective view of a rolling device described in at least one embodiment herein.

In still other embodiments, as shown in FIG. 9, the rolling device 300d described herein may include a third slit 350d which may extend vertically, generally perpendicular to the longitudinal axis of the channel 307d. The third slit 350d extends through a sidewall of the fin 330d and a sidewall of the tubular body 305d. By extending through one entire side of the device 300d, including the sidewalls of the tubular body 305d and the fin 330d, the tie handle of the central tie can be easily transferred into the inside of the device 300d for faster loading of the implantable sheet and the delivery tool into the channel 307d.

As further depicted in FIG. 9, in some embodiments, the elongate body and thus the channel 307d and first slit 315d are discontinuous and do not extend completely across the entire length of the device creating open spaces 360d between portions of the elongate body 305d. Also, in some embodiments, the rolling device may not include a spout or flange extending from a distal end portion thereof.

The fins as described herein are configured to be a handle for the surgeon to use when handling the rolling device. The fin cavities, of the fins described herein, participate in the global flexibility of the rolling device, to compress or relax the rolled implantable sheet and the delivery tool inside the channel of the rolling device.

The rolling device can be made of any suitable material. Some non-limiting examples of suitable materials include polyethylene, polypropylene, polyamides, polyaryl ether ketone (PAEK), acrylonitrile butadiene styrene (ABS), polyether ether ketone (PEEK), polyoxymethylene (POM), nitinol (NiTi), polyetherimide (PEI), polycarbonates (PC), and combinations thereof.

In addition to the various rolling devices described hereinabove, in some embodiments, the rolling device is a rolling device described in any of U.S. Pat. Nos. 8,317,808; 8,734,473; 9,364,311; 10,052,126; and 10,016,265, each of which are incorporated herein by reference.

In some embodiments, the implantable sheet is an implantable mesh and the rolling device is a mesh rolling device.

In some embodiments, the implantable sheet is an implantable mesh, the central tie is a suture, the flexible delivery tool is a mesh delivery tool, and the rolling device is a mesh rolling device.

VI. Insertion Member

The insertion members described herein are configured to connect or attach to the proximal end of the delivery tool. Once attached, the insertion members are designed to rotate the delivery tool causing the implantable sheet to wrap around the exterior of the delivery tool into a rolled configuration. Therefore, the insertion member provides a dual ability or function for both rolling and inserting of the implantable sheet and the delivery tool.

Figure 10A:
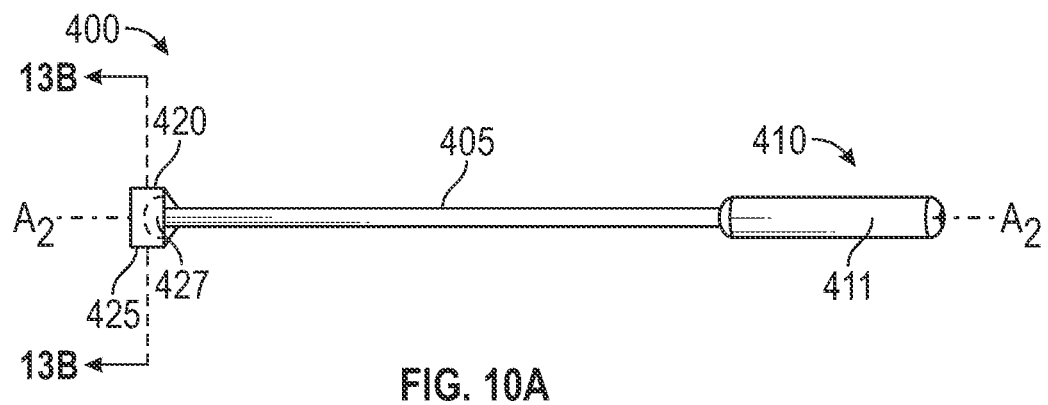
FIGS. 10A-10B include a side view and an end view, respectively, of an insertion member described in at least one embodiment herein.

FIG. 10A depicts an insertion member 400 having an elongate body 405 extending between a proximal end portion 410 and distal end portion 420 of the insertion member 400. The proximal end portion 410 of the insertion member 400 includes a handle or grip 411 designed to assist with moving the insertion member 400 longitudinally through the trocar and also with rotating of the insertion member 400 which in turn rotates the delivery tool inside the rolling device. The distal end portion 420 of the insertion member may include a socket 425 designed to mate with the proximal end portion of the delivery tool.

Figure 10B:
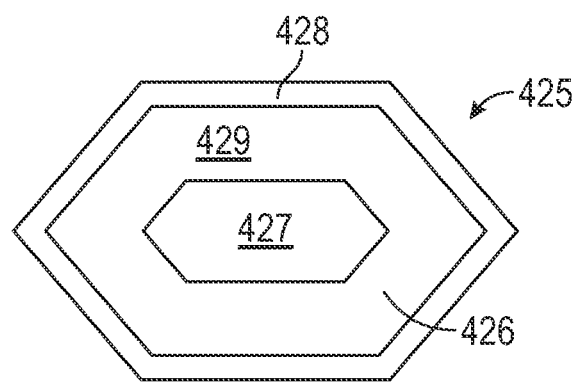

As shown in FIG. 10B, the socket 425 including a socket cavity 426 having an inner perimeter which matches the outer perimeter of the shaped proximal end portion of the delivery tool. The socket cavity 426 may also include a socket protrusion 427 positioned within the cavity 426 which mates and/or properly sits within the opening on the proximal end of the delivery tool. When attached, the insertion member 400 and the delivery tool share a common central longitudinal axis $A_2$. The insertion member 400 has a length that is longer than a typical trocar used for laparoscopic surgery. In some instances, the insertion member has a length that is longer than a trocar and a rolling device as described herein combined.

FIG. 10B shows an end view into the socket on the distal end portion 420 of an insertion member 400 along the longitudinal axis $A_2$. The socket 425 shown is configured to matingly engage with the hexagonal shaped proximal end of FIG. 2B. The socket 425 includes a socket cavity 426 having a shape or contour which mirrors the shaped proximal end portion 210a of a delivery tool 200. The socket cavity 426 including at least one sidewall 428 and a base 429 which together define the cavity 426. As shown, in some embodiments, the base 429 may further include a socket protrusion 427 configured to matingly engage and/or properly sit within the opening on the proximal end of the delivery tool. The protrusion having a shape or contour which mirrors the shape or contour of the opening of the lumen on the proximal end of the delivery tool to ensure proper sitting or mating.

Although shown as specifically hexagonal, each of the shaped proximal end of the delivery tool, the opening in the proximal end of the lumen of the delivery tool, the socket, and the socket protrusion may be of any shape or contour suitable for securing the insertion member to the delivery tool. In some embodiments, the shapes or contours of the shaped proximal end of the delivery tool and the socket are different from the shapes or contours of the opening in the proximal end of the lumen and the socket protrusion.

The insertion member can be made of any suitable material. Some non-limiting examples of suitable materials include polyethylene, polypropylene, polyamides, polyaryl ether ketone (PAEK), acrylonitrile butadiene styrene (ABS), polyether ether ketone (PEEK), polyoxymethylene (POM), nitinol (NiTi), polyetherimide (PEI), polycarbonates (PC), and combinations thereof.

VII. Sheet-Tool Assembly

Figure 11A:
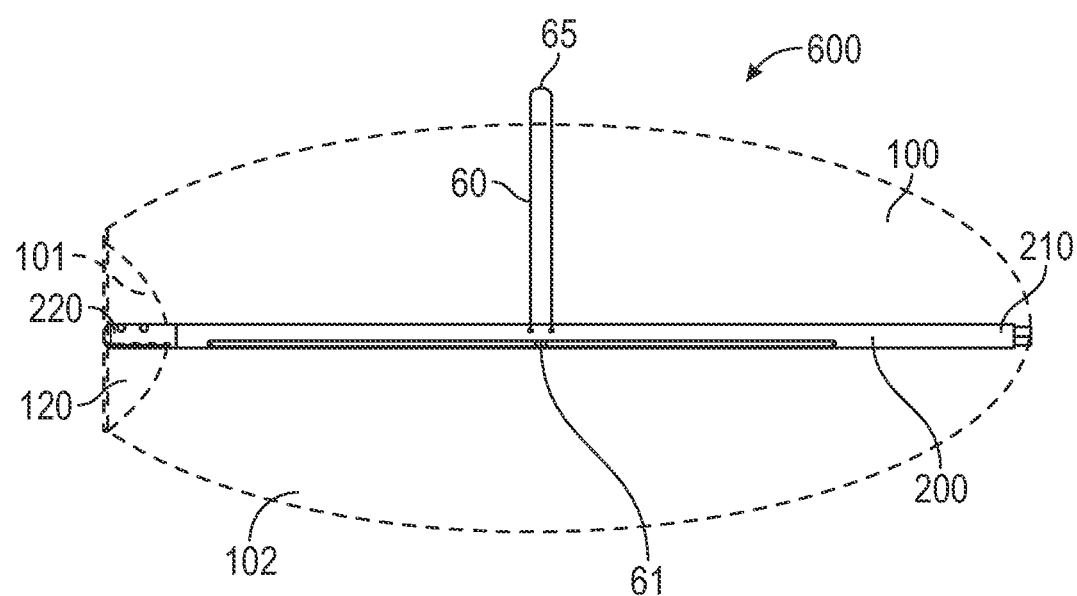
FIGS. 11A-11B include top views of a sheet-tool assembly described in at least one embodiment herein.
Figure 11B:
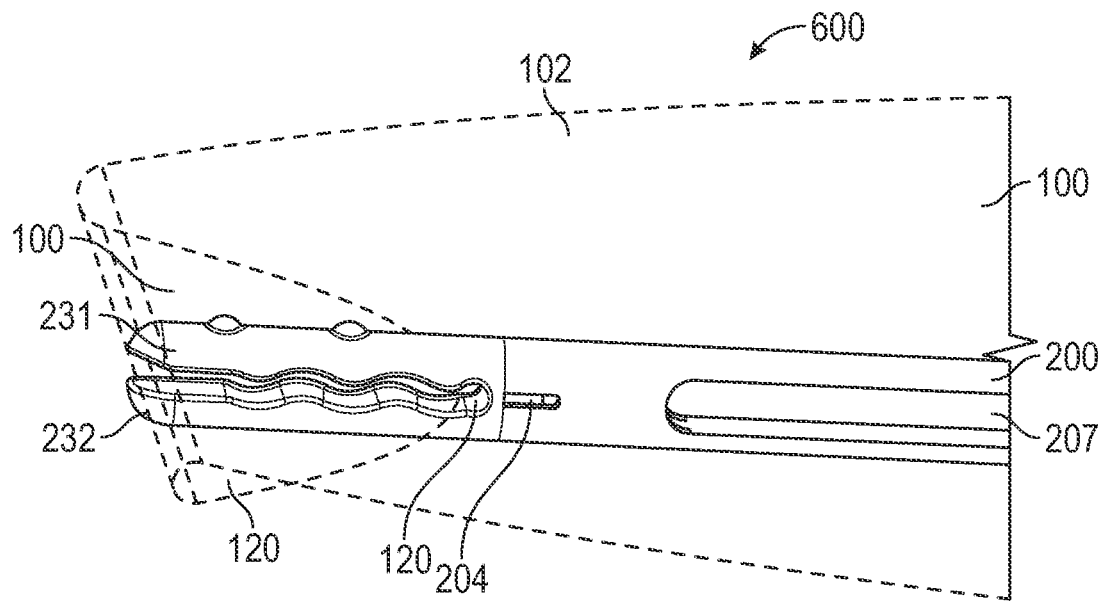

In FIGS. 11A-11B, a sheet-tool assembly 600 is depicted including an implantable sheet 100, such as a mesh, a delivery tool 200, and a central tie 60. The implantable sheet 100 is shown in phantom for clarity purposes. A first face 101 of an implantable sheet 100 is shown facing and/or connected to the delivery tool 200 and a second face 102 opposite the first face 101 of the implantable sheet 100 is shown facing away from the delivery tool 200. A distal portion 120 of the first opposite face 101 of the implantable sheet 100 is shown folded proximally over one of the upper or lower jaw members 231, 232, and secured within the slot 230 of the delivery tool 200. The central tie 60 forms a first loop 60 in the lumen of the delivery tool 200 and a tie handle 65 in the form of a second loop extending through the tie holes 202 and the implantable sheet 100, particularly a central portion of the sheet 100.

The sheet-tool assembly may include any combination of the various details described herein relating to the delivery tool and the implantable sheet. For example, although not specifically shown in FIGS. 11A-11B, in some embodiments, the sheet-tool assembly may further include at least one of a central tie, a suture aperture, and/or a looped suture extending therefrom, as described herein.

Figure 11C:
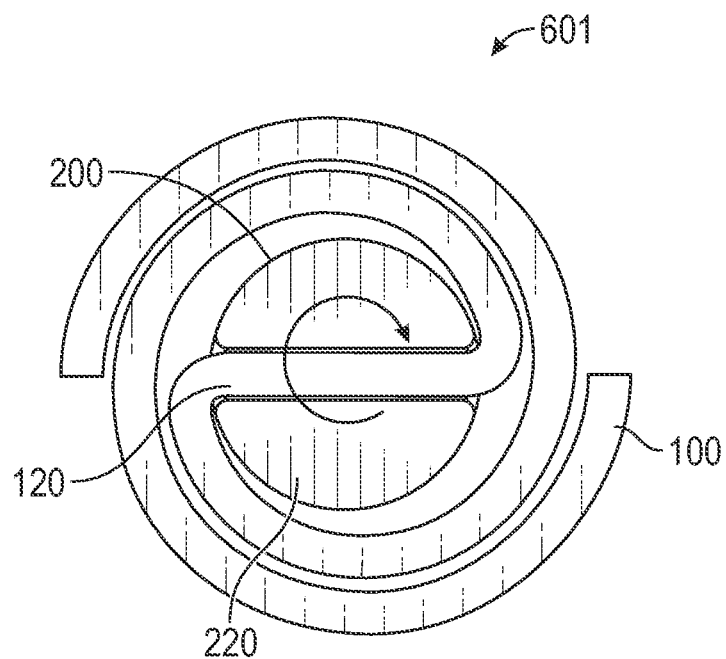
FIG. 11C is a schematic end view of the sheet-tool assembly of FIGS. 11A-11B in a rolled configuration described in at least one embodiment herein.

As shown in FIG. 11C, when the sheet-tool assembly 600 is rolled to form a rolled sheet-tool assembly 601, the sheet 100 is rolled closely around the outer surface of the delivery tool 200 without the delivery tool insert included in the delivery tool. Although not shown in FIG. 11C, when the sheet-tool assembly is rolled, the handles of the central tie wrap around the outer surface of the rolled sheet-tool assembly thereby maintaining the implantable sheet in a rolled configuration around the delivery tool.

In some embodiments, the implantable sheet is an implantable mesh combined with the delivery tool described herein (without the delivery tool insert) to form a mesh-tool assembly. In some embodiments, the mesh-tool assembly can be rolled as described herein to form a rolled mesh-tool assembly.

The sheet-tool assembly or mesh-tool assembly may be preassembled within the package or may be post-assembled after the package is opened and the components accessed.

VIII. Rolled Sheet-Tool-Insert Assembly

After the implantable sheet is rolled about the delivery tool to form the rolled sheet-tool assembly, the delivery tool insert can be inserted into the lumen of the delivery tool to form a rolled sheet-tool-insert assembly. The delivery tool insert is inserted into the delivery tool in a narrow configuration wherein the one or more resilient arms are narrowed to enter the lumen of the delivery tool. Prior to implantation, the delivery tool insert is maintained in the narrowed configuration by any combination of the rolling device, the rolled implantable sheet, and/or the central tie wrapped closely around the rolled sheet.

IX. Methods of Use

The present disclosure also provides methods of treating or repairing soft tissue defects with the use of the various components of the kits described herein. The kits and components described herein are intended to be used in any variety of surgical procedures wherein a soft tissue defect needs repair. In some embodiments, the kits and components described herein may be used to repair various types of hernia including but not limited to hernia repair using an IPOM (i.e. intraperitoneal), TAPPS (i.e., preperitoneal), or TEPS (i.e., extraperitoneal) technique.

Any methods described herein directed to repairing a soft tissue defect or hernia is intended to be applicable specifically to ventral hernia repair and/or ventral hernia repair using an IPOM surgical technique.

As provided in FIGS. 12A-13G, in some embodiments, methods for repairing a soft tissue defect, such as a hernia or ventral hernia may include: preparing a rolled sheet-tool-insert assembly, inserting the rolled sheet-tool-insert assembly into the patient, orienting the implantable sheet, deploying the implantable sheet, positioning and fixating the implantable sheet, detaching the sheet from the delivery tool, the delivery tool insert, and central tie, and removing the central tie and the delivery tool including the delivery tool insert from the patient.

Figure 12A:
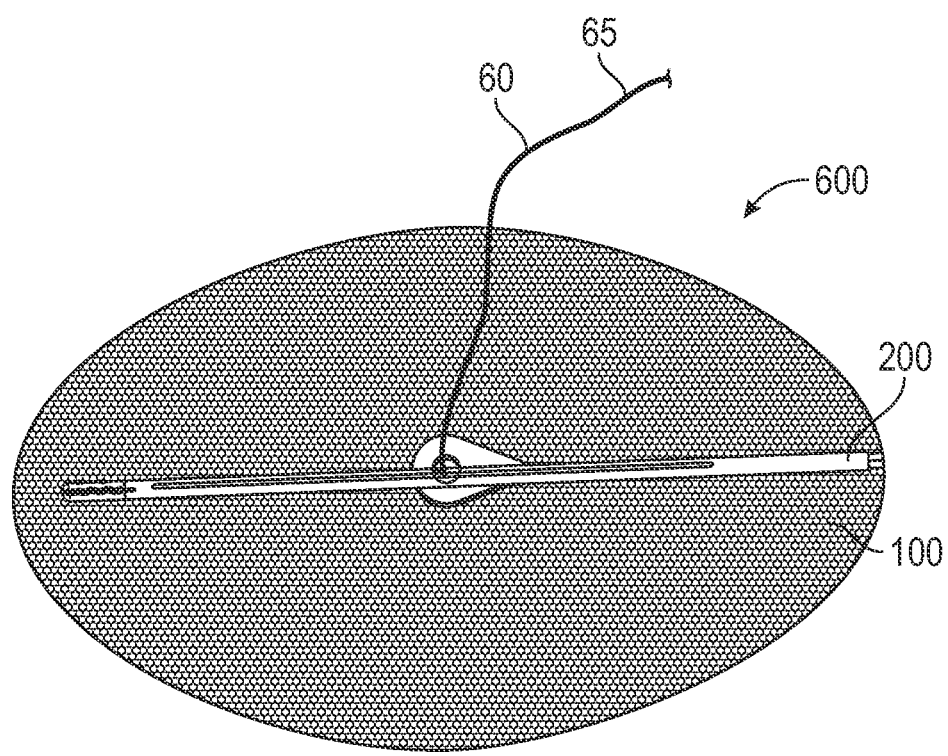
FIGS. 12A-12E are top views of a sheet-tool assembly and rolled sheet-tool assembly described in at least one embodiment herein.
Figure 12B:
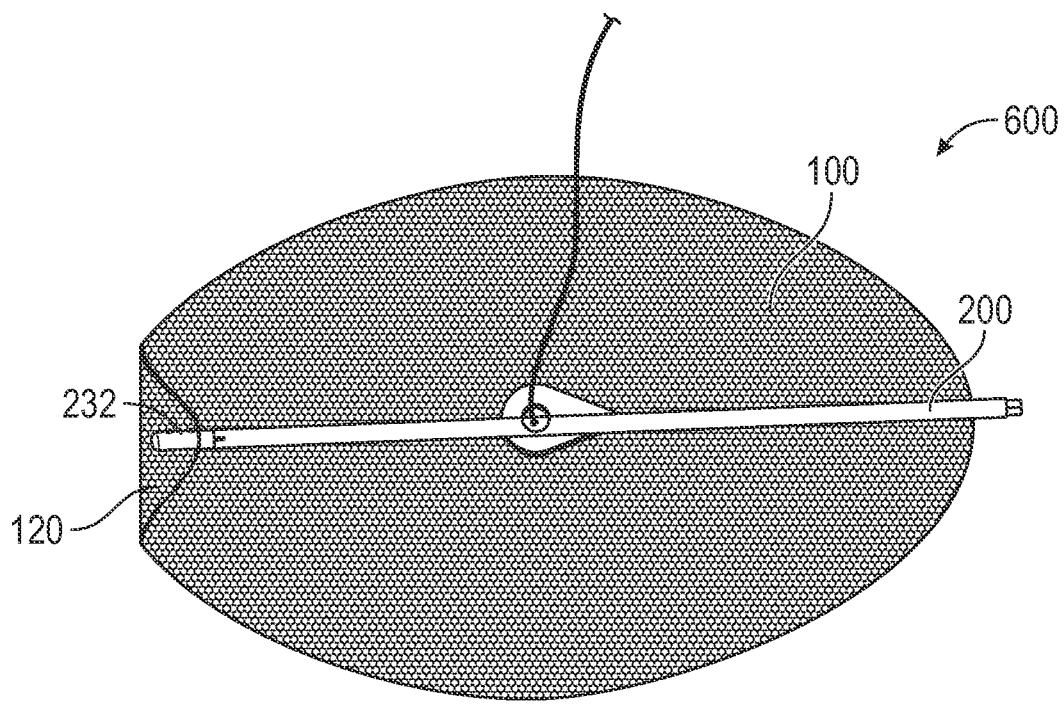

As depicted in FIGS. 12A-12B, a sheet-tool assembly 600 is formed wherein a handle 65 of a central tie 60 extends from a central portion of an implantable sheet 100 and a delivery tool 200, and a distal end portion 120 of the implantable sheet 100 is folded over one of an upper or lower jaw members 231, 232 of the delivery tool 200 and secured within a slot 230 defined within a distal end 220a of the delivery tool 200.

Figure 12C:
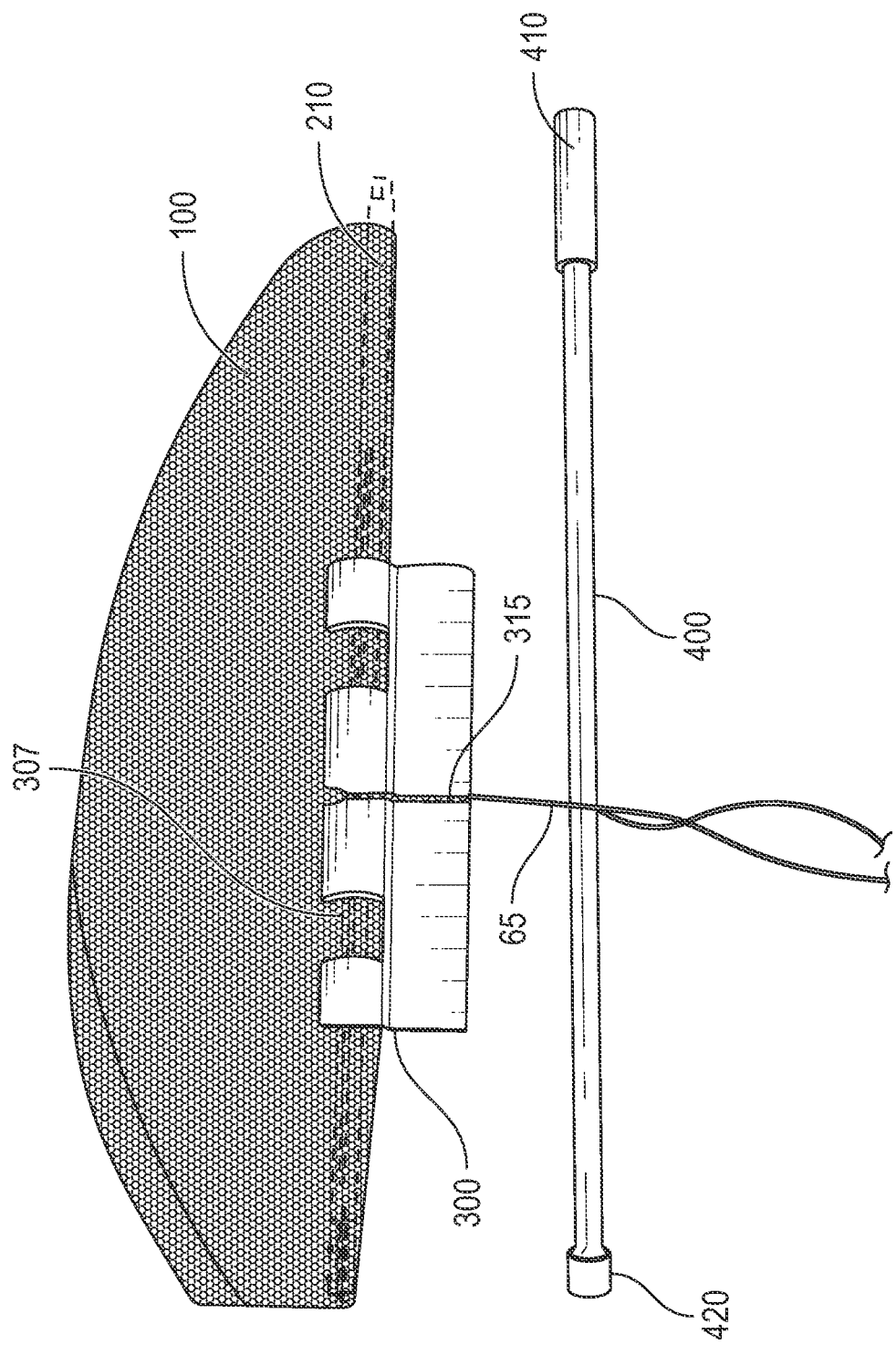
Figure 12D:
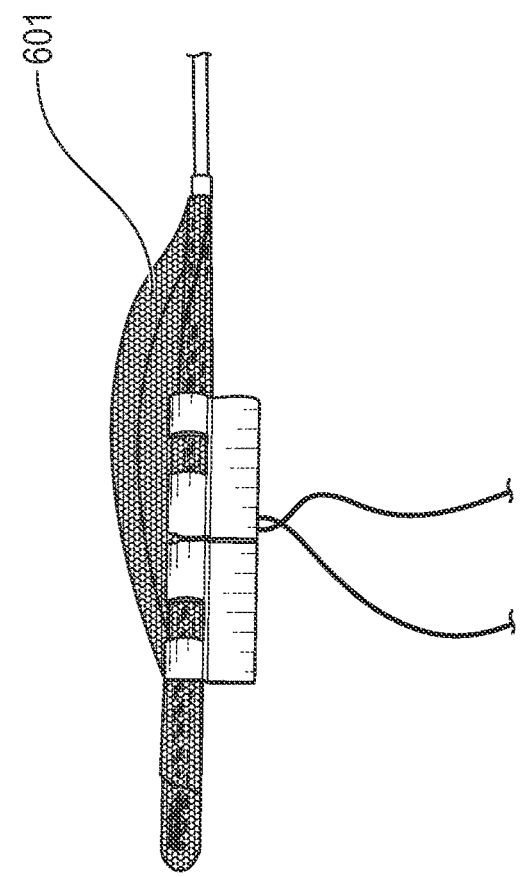
Figure 12D:
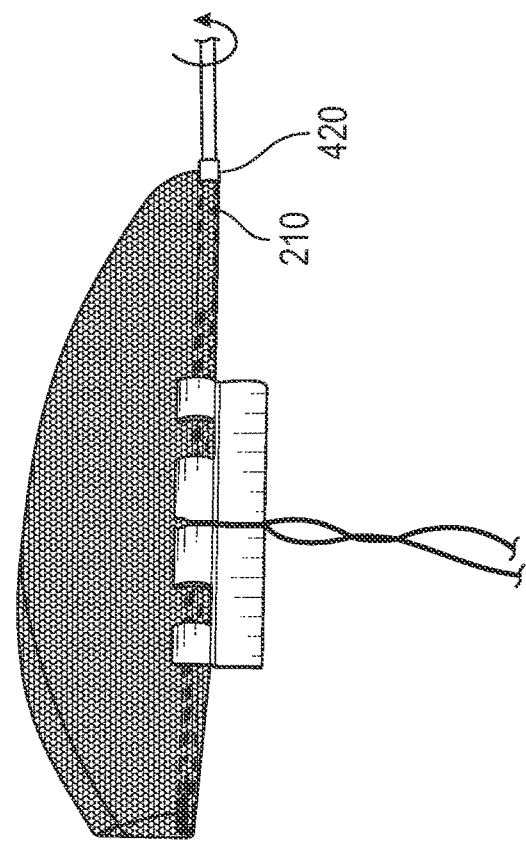

As depicted in FIGS. 12C-12D, the implantable sheet 100 of the sheet-tool assembly 600 can then be rolled to form a rolled sheet-tool assembly 601. The handle 65 of the central tie 60 can be positioned within a slit 350 extending generally perpendicular to a longitudinal channel 307 of the rolling device 300, where upon pulling of the handle 65 draws the sheet-tool assembly 600 into the channel 307 of the rolling device 300. A distal end 420 of an insertion member 400 can be secured to a proximal end 210a of the delivery tool 200 to rotate (see arrow in FIG. 12D) the delivery tool 200 within the rolling device 300 thereby causing the sheet 100 to be rolled upon an outer surface of the delivery tool 200 to form a rolled sheet-tool assembly 601.

Figure 12E:
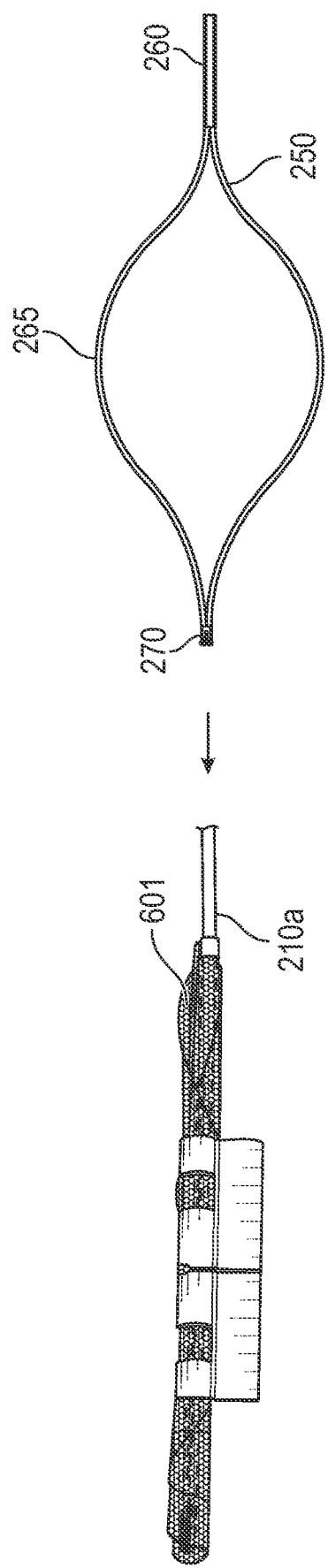
Figure 12F:
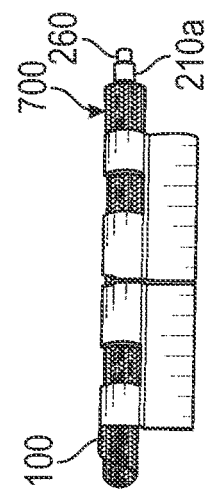
FIG. 12F is a top view of a rolled sheet-tool-insert assembly described in at least one embodiment herein.

Once the rolled sheet-tool assembly 601 is formed, as shown in FIG. 12E, the insertion member 400 is removed from the rolled sheet-tool assembly 601 and a delivery tool insert 250 as described herein and including one or more resilient arms 265 is inserted (see arrow in FIG. 12E) into a lumen defined within the proximal end 210a of the delivery tool 200 to form a rolled sheet-tool-insert assembly 700 within the rolling device, as depicted in FIG. 12F.

Once the sheet is prepared in a rolled configuration and the rolled sheet-tool-insert assembly 700 is prepared within the rolling device 300, the rolled sheet-tool-insert assembly 700 can be inserted into an abdominal cavity of a patient. For example, as shown in FIGS. 13A-13F, in some embodiments, a method of inserting a rolled sheet-tool-insert assembly 700 is described and includes the steps of: attaching a distal end 320 of the rolling device 300 to a trocar 810 extending from the patient's body 805, such as the abdomen; and moving or pushing the insertion member 400 in a distal direction through the channel 307 of the rolling device 300 and into the trocar 810 until the delivery tool 200 (including the delivery tool insert 250) including the implantable sheet 100 in a rolled configuration or the rolled sheet-tool-insert assembly 700 completely enters a cavity 800 within the patient, such as the abdominal cavity 800. In some embodiments, the rolling device 300 and the insertion member 400 can be used as handles during the insertion process to carry the rolled sheet-tool-insert assembly from the package to the trocar 810. A surgeon can easily grab the rolling device 300 on one end and the insertion member 400 on an opposite end, with the rolled sheet-tool-insert assembly positioned therebetween, to perform inserting the rolled sheet-tool-insert assembly into the patient. Since the rolling device 300 and the insertion member 400 are not intended to enter the patient contact does not need to be avoided. This design also prevents or limits the amount of direct contact with the implantable sheet and the delivery tool thereby reducing the likelihood of contamination.

Figure 13A:
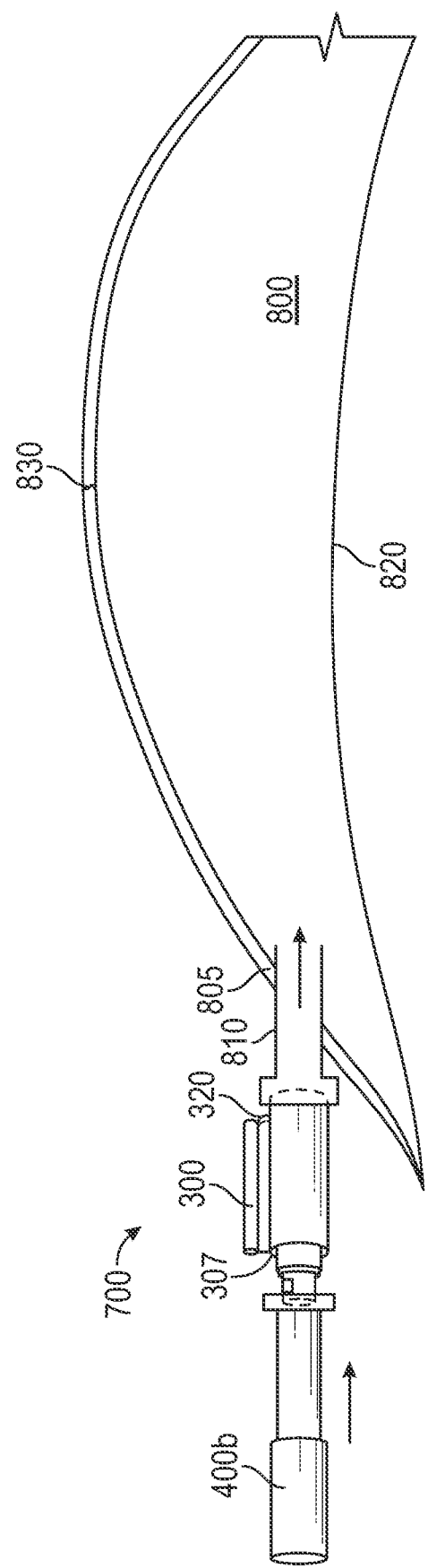
Figure 13B:
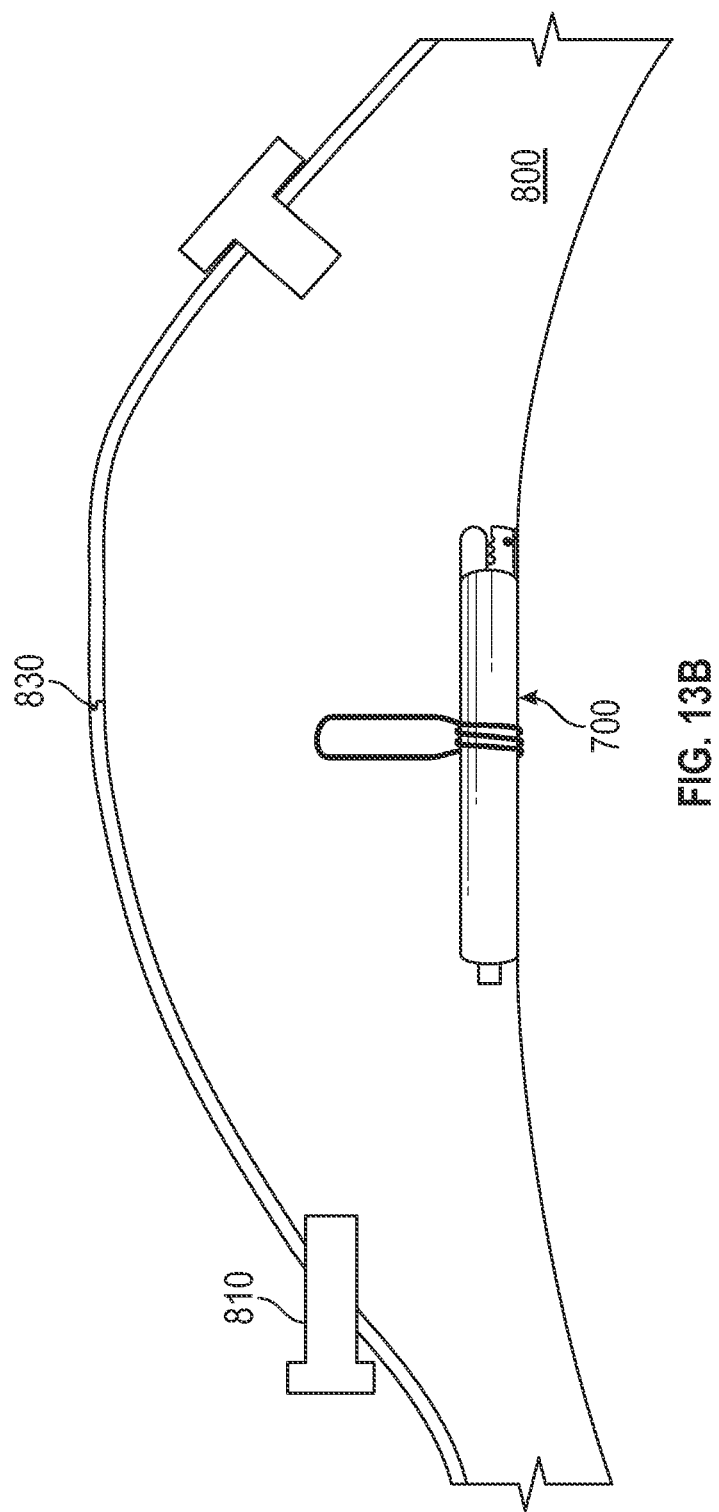
Figure 13C:
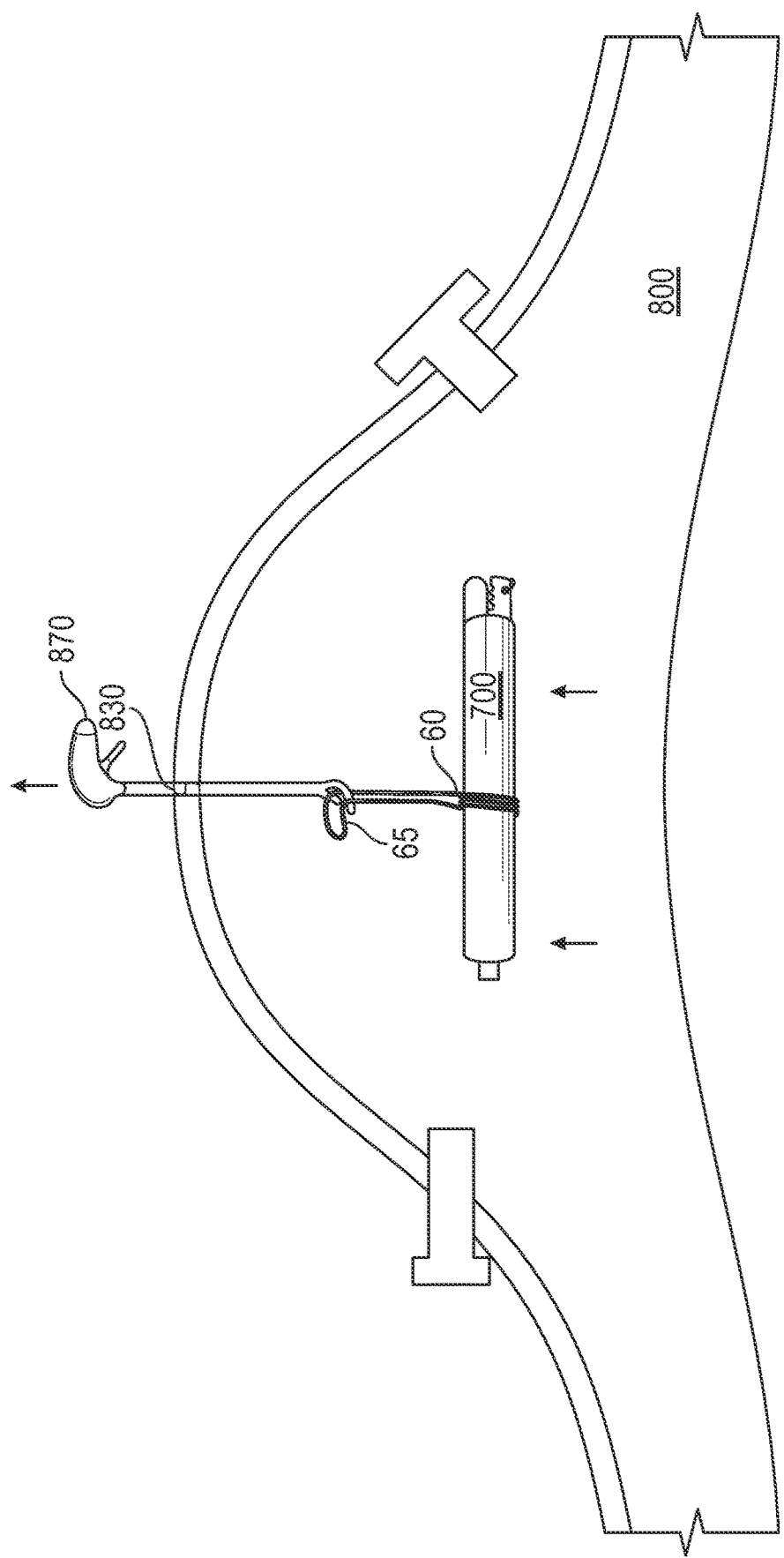
Figure 13D:
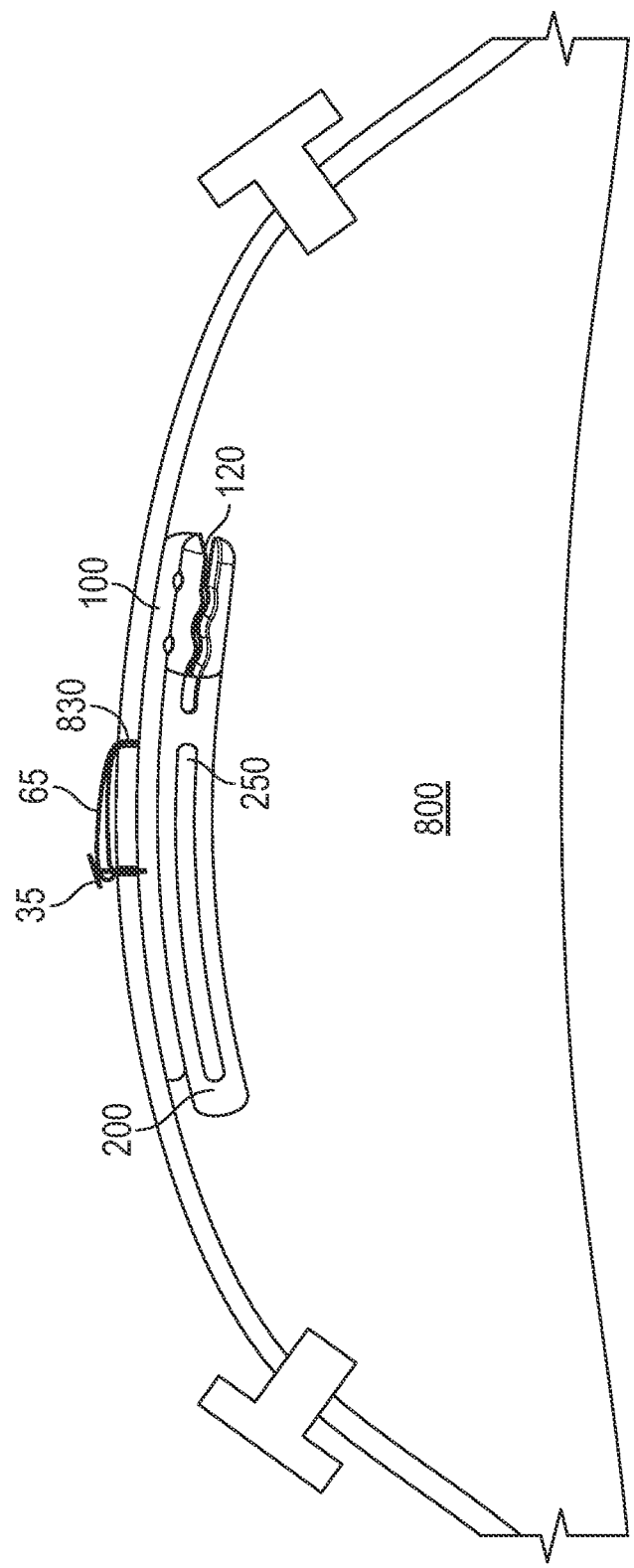
Figure 13E:
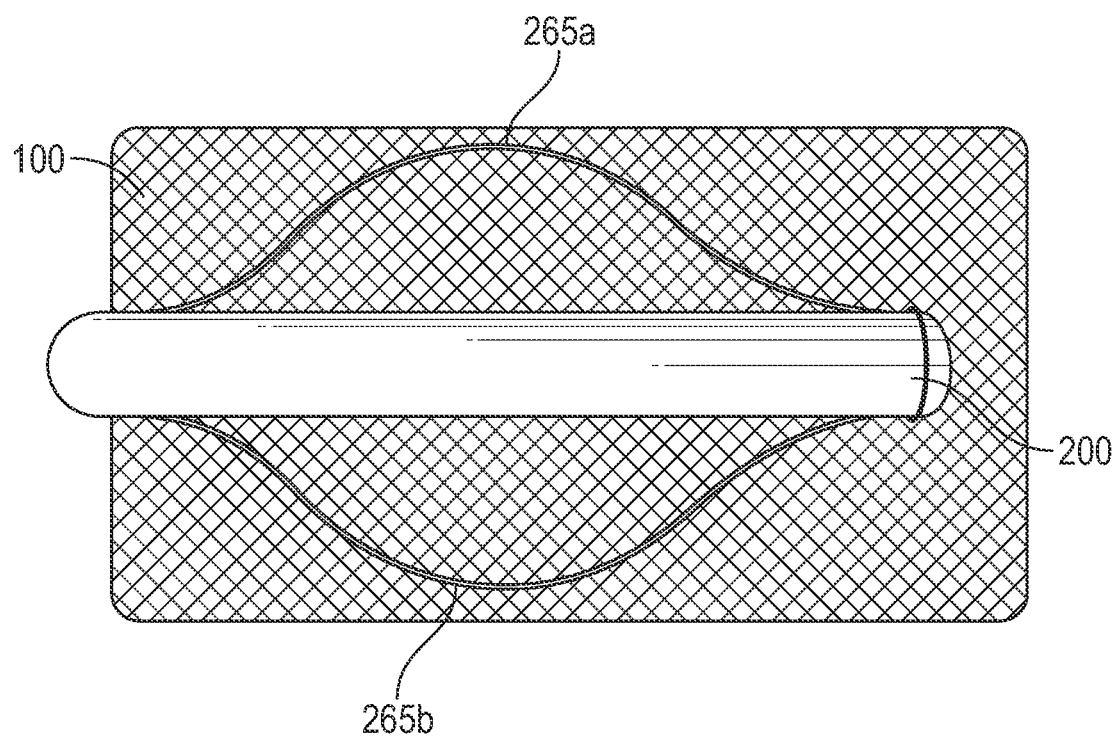

Following insertion, as shown in FIG. 13B, the rolled sheet-tool-insert assembly 700 is free of both the rolling device 300 and the insertion member 400. However, the rolled sheet-tool-insert assembly 700 is still in a rolled configuration and needs to be deployed within the cavity 800 of the patient. For example, as shown in FIGS. 13C-13E, in some embodiments, a method of deploying the rolled implantable sheet or rolled sheet-tool-insert assembly 700 is described and includes the steps of: introducing a suture catcher 870, such as an Endoclose™, into the patient or body cavity 800 by penetrating through a center of the soft tissue defect or hernia 830 from outside the patient or body cavity; grasping the tie handle 65 of the central tie 60 extending from the rolled sheet-tool-insert assembly 700; pulling the tie handle 65 back through the tissue defect or hernia 830 to the outside of the patient thereby releasing the rolled sheet 100 or rolled sheet-tool-insert assembly 700 of constraint by the tie handle 65; and securing the tie handle 65 outside the patient cavity 800. The tie handle 65 can be secured outside the patient with any type of fastener 35. Because the delivery tool 200 (including the delivery tool insert 250) is still attached to the sheet 100 via the central tie 60, the pulling of the tie handle 65 out through the tissue defect or hernia 830, forces the delivery tool 200 (including the delivery tool insert 250) against the underside of the tissue defect or hernia 830 with the sheet 100 positioned therebetween. The combination of the central tie 60 and the delivery tool 200 lifts and holds the sheet 100 up against the underside of the tissue defect 830. Since the tie handle 65 is no longer wrapped around the sheet 100, the delivery tool 200, and the delivery tool insert 250, the rolled mesh 100 begins to start to unroll and the one or more resilient arms 265a, 265b will naturally expand outwardly through the one or more windows 207 of the delivery tool 200 forcing the sheet 100 to flatten against the abdominal cavity tissue. During deployment or the method of deploying the implantable sheet, the distal portion 120 of the sheet 100 remains secured within the slot 230 of the delivery tool 200. In addition, by passing the suture catcher 870 through the center of the defect 830, the final placement of the sheet 100 is likely to also be centered on the defect 830.

Figure 13F:
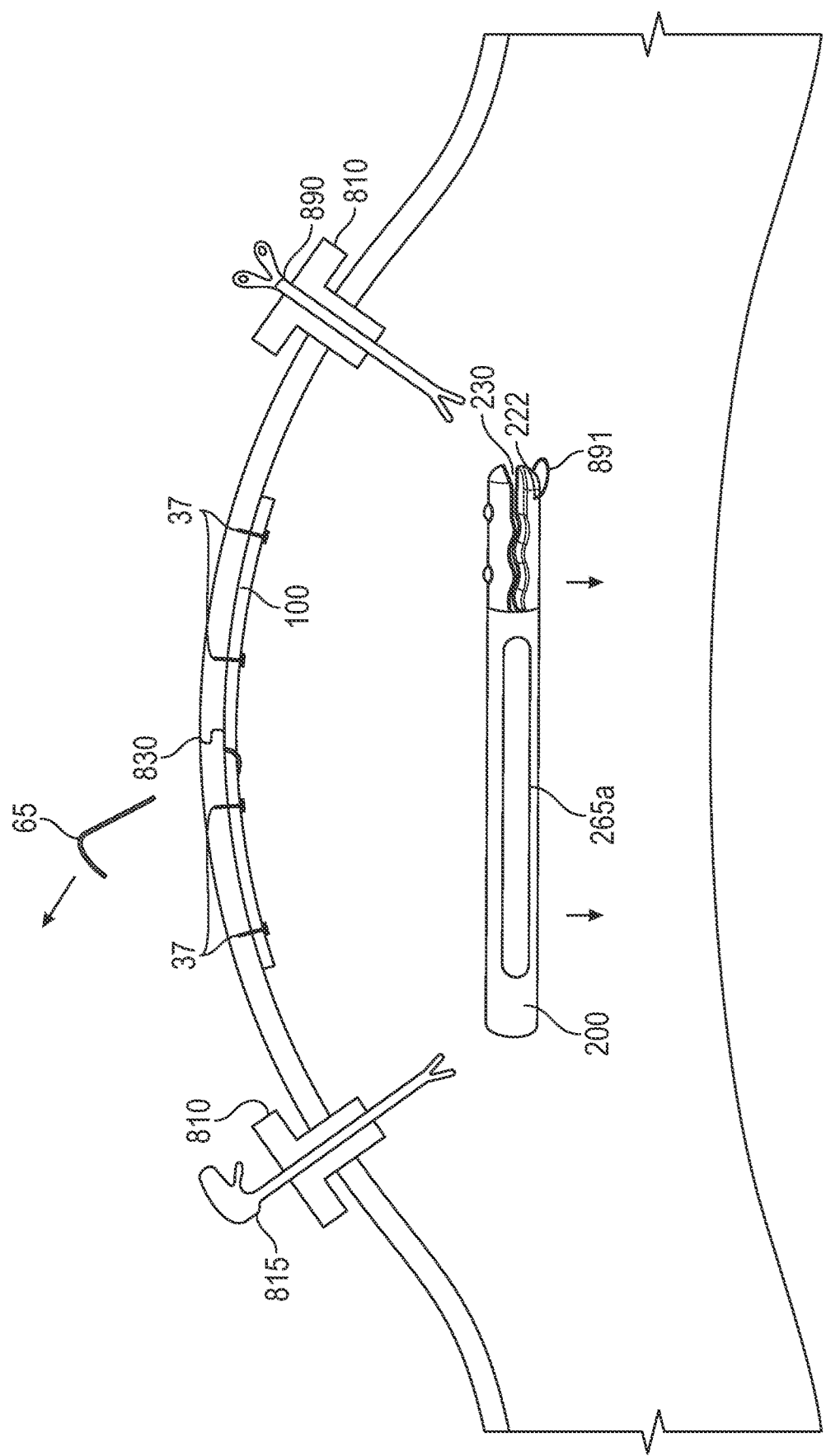

Following deployment, final placement and/or positioning of the sheet can be determined and the sheet can be fixated in or around the tissue defect or hernia. For example, in some embodiments, as shown in FIG. 13F, a method of placing and fixating the implantable sheet is described and includes the steps of: manipulating the sheet 100 into a final position with a laparoscopic surgical grasper 875; and fixating the sheet 100 into tissue in or around the tissue defect 830 while the resilient arms 265a, 265b of the delivery tool insert 250, the delivery tool 200 and the central tie 60 maintain the sheet 100 up against the underside of the defect 830. Any standard laparoscopic surgical grasper or standard surgical fastening device 875, such as a tack or clip applier, stapler, or suturing device, may be introduced into the patient or a cavity within a patient, such as the abdominal cavity, via one or more trocars. Because the sheet 100 remains suspended up against the defect while being positioned and/or fixated, both hands of the surgeon are free to work in unison to position and fixate the implantable sheet to the tissue. The sheet can be fixated using any suitable fixation means 37, including, but not intended to be limited to, sutures, clips, tacks, staples, adhesives, and the like. During positioning and/or fixating of the sheet, the distal portion 120 of the mesh 100 can either remain secured within the slot 230 of the delivery tool 200 or be freed of the delivery tool 200 and fixated to the tissue.

Following fixation of the implantable sheet 100, the delivery tool 200 (including the delivery tool insert 250) and the central tie 60, including the tie handle 65, can be separated from the sheet 100 and withdrawn from the patient's body 800. For example, as shown in FIGS. 13F-13G, in some embodiments, a method of withdrawing the delivery tool 200 (including the delivery tool insert 250) and central tie from the site of implantation is described and includes the steps of: freeing the sheet 100, and particularly the distal portion 120 of the sheet, from the slot 230 defined within the distal end portion of the delivery tool 200; cutting one filament of the tie handle 65 secured outside the patient, thus freeing the central tie 60 from both the delivery tool 200 (including the delivery tool insert 250) and the sheet 100; and withdrawing the delivery tool 200 (including the delivery tool insert 250) and central tie 60 from inside the patient. In some embodiments, the laparoscopic surgical grasper 890 can be utilized to free the slot 230 in the distal end portion of the delivery tool 200 from the sheet 100. The grasper 890 can also be used to grab the distal end of the delivery tool 200 (including the delivery tool insert 250), and particularly a looped suture 891 positioned through the suture aperture 222 on the distal end portion of the delivery tool 200, to slide the distal end portion 220 of delivery tool 200 (including the delivery tool insert 250) away from the distal portion 120 of the sheet 100 thereby removing the sheet 100 from the delivery tool 200. The delivery tool 200 (including the delivery tool insert 250) can then be withdrawn or retrieved from inside the patient by using the grasper 890 to grab the looped suture 891 on the distal end of the tool 200 (including the delivery tool insert 250) and withdrawing the tool 200 (including the delivery tool insert 250) back through the trocar 810 and out of the patient. Since the delivery tool insert 250 is still locked in place within the lumen 206 of the delivery tool 200, the resilient arms 265a, 265b will be forced to retract by the walls of the trocar 810, as the delivery tool 200 (including the delivery tool insert 250) is pulled out through the trocar 810. Because the delivery tool is flexible, the delivery tool does not need to be perfectly aligned with the trocar to be removed. In the event any portion of the central tie remains inside the cavity after cutting, the grasper may also be used to withdraw the central tie.

Each of the components and/or kits described herein may be stored in any package suitable for maintaining the components and/or kits under sterile conditions. Some non-limiting examples includes peelable packaging, foil packaging, Tyvek packaging, plastic molded packaging, and the like.

In some embodiments, a surgical kit for hernia repair is described including an implantable sheet, a delivery tool and a delivery tool insert. The implantable sheet, such as an implantable mesh, includes a first and second opposite face. The delivery tool includes an elongate body extending between a proximal end portion and a distal end portion, the elongate body including a lumen extending therethrough and at least one window defined in a sidewall of the elongate body, the window configured to allow access to the lumen from a side of the elongate body. The delivery tool insert is configured to be received within the lumen of the elongate body, the delivery tool insert including a proximal end portion, a distal end portion, and at least one resilient arm extending therebetween, the at least one resilient arm configured to extend through the at least one window when aligned therewith.

In some embodiments, the proximal end portion and the distal end portion of the delivery tool insert define a longitudinal axis with the one or more resilient arms connecting the proximal end portion to the distal end portion, wherein the one or more resilient arms display a natural bias to extend away from the longitudinal axis.

In some embodiments, the one or more resilient arms of the delivery tool insert include a pair of resilient arms which naturally form a generally circular or eye-shaped opening therebetween.

In some embodiments, the distal end portion of the delivery tool insert further comprises at least one locking member extending therefrom and the distal end portion of the delivery tool further comprises at least one locking recess defined therethrough, the locking member configured to be secured in the at least one locking recess when aligned therewith, to lock the delivery tool insert within the lumen of the delivery tool.

In some embodiments, the distal end portion of the delivery tool further includes a slot separating the distal end portion of the delivery tool into an upper and lower jaw member, the slot configured to secure a distal end portion of the implantable sheet between the upper and lower jaw members.

In some embodiments, the delivery tool further includes a central tie connecting the delivery tool to the implantable sheet or mesh, wherein the central tie passes through a pair of tie holes defined through a central portion of the elongate body of the delivery tool forming a loop inside the lumen of the delivery tool and extending away from the delivery tool through the second face of the sheet or mesh and forming a handle extending away from the opposite first face of the sheet or mesh.

In some embodiments, the distal end portion of the delivery tool further comprises a suture aperture defined therethrough, the suture aperture configured to receive a looped material or suture suitable for grasping when withdrawing the delivery tool from the patient.

In some embodiments, the distal end portion of the delivery tool further includes at least one crenulation extending outwardly from an outer surface of the distal end portion, the crenulation configured to engage openings in the implantable sheet when rolled thereon.

In some embodiments, the surgical kits described herein further include a rolling device configured to roll the implantable sheet around the outer surface of the delivery tool.

In some embodiments, the surgical kits described herein further include an insertion member including an elongate body extending between a proximal end portion including a handle and a distal end portion including a socket, the socket configured to matingly engage the proximal end of the delivery tool.

In some embodiments, a two-piece sheet or mesh delivery device is described including a delivery tool and a delivery tool insert. The delivery tool includes an elongate body extending between a proximal end portion and a distal end portion, the elongate body including a lumen extending therethrough and a pair of windows defined in a sidewall of the elongate body, the pair of windows configured to allow access to the lumen from outside of the elongate body. The delivery tool insert configured to be received within the lumen of the elongate body, the delivery tool insert including a proximal end portion, a distal end portion, and a pair of resilient arms extending therebetween, the pair of resilient arms configured to extend through the pair of windows when aligned therewith, wherein the two-piece delivery device is configured to transition between a narrowed configuration, under stress, and an expanded configuration, under no stress.

In some embodiments, the proximal end portion and the distal end portion of the delivery tool insert, of the two-piece delivery tool, define a longitudinal axis therebetween and the pair of resilient arms display a natural bias to extend away from each other and the longitudinal axis.

In some embodiments, the distal end portion of the delivery tool insert, of the two-piece delivery tool, further includes at least one locking member extending therefrom and the distal end portion of the delivery tool, of the two-piece delivery tool, further includes at least one locking recess defined therethrough, the locking member configured to be secured in the at least one locking recess when aligned therewith, to lock the delivery tool insert within the lumen of the delivery tool forming the two-piece delivery device.

In some embodiments, the distal end portion of the delivery tool, of the two-piece delivery device, further includes a slot separating the distal end portion of the delivery tool into an upper and lower jaw member, the slot configured to secure a distal end portion of the implantable sheet or mesh between the upper and lower jaw members.

In some embodiments, the two-piece delivery device further includes a pair of tie holes defined through a central portion of the elongate body of the delivery tool configured to receive a central tie therethrough.

In some embodiments, the distal end portion of the delivery tool, of the two-piece delivery device, further includes a suture aperture defined therethrough, the suture aperture configured to receive a looped suture suitable for grasping when withdrawing the delivery tool from the patient.

In some embodiments, a method of repairing a hernia, and particularly a ventral hernia, including: combining an implantable sheet or mesh, a central tie, and a delivery tool to form a sheet-tool assembly, the delivery tool including an elongate body extending between a proximal end portion and a distal end portion, the elongate body including a lumen extending therethrough and at least one window defined in a sidewall of the elongate body, the window configured to allow access to the lumen from a side of the elongate body; preparing the sheet-tool assembly for insertion into a patient by using a rolling device to form a rolled sheet-tool assembly; inserting a delivery tool insert into the lumen of the delivery tool to form a rolled sheet-tool-insert assembly, the delivery tool insert including a proximal end portion, a distal end portion, and at least one resilient arm extending therebetween, the at least one resilient arm configured to extend through the at least one window when aligned therewith; inserting the rolled sheet-tool-insert assembly into a patient via a trocar using the rolling device; deploying the sheet or mesh inside the patient; positioning and fixating the sheet inside the patient; and withdrawing the delivery tool including the delivery tool insert from the patient.

It will be understood that various modifications may be made to the embodiments disclosed herein. Thus, those skilled in the art will envision other modifications within the scope and spirit of the disclosure.

What is claimed is:

1. A two-piece implantable sheet delivery device comprising:
   a delivery tool including an elongate body extending between a proximal end portion and a distal end portion, the elongate body including a lumen extending from the proximal end portion through a central portion towards the distal end portion of the elongate body and a pair of windows defined in a sidewall of the elongate body, the pair of windows configured to allow access to the lumen from outside of the elongate body, and,
   a delivery tool insert configured to be received within the lumen of the elongate body, the delivery tool insert including a proximal end portion, a distal end portion, and a pair of resilient arms extending therebetween, the proximal and distal end portions of the delivery tool insert configured to be received within the lumen of the elongate body, the pair of resilient arms configured to extend through the pair of windows when aligned therewith, wherein the two-piece implantable sheet delivery device is configured to transition between a restrained configuration and an expanded configuration.

2. The two-piece implantable sheet delivery device of claim 1, wherein the proximal end portion and the distal end portion of the delivery tool insert define a longitudinal axis therebetween and the pair of resilient arms display a natural bias to extend away from each other and the longitudinal axis.

3. The two-piece implantable sheet delivery device of claim 1, wherein the pair of resilient arms of the delivery tool insert naturally form a generally circular shaped opening therebetween.

4. The two-piece implantable sheet delivery device of claim 1, wherein the distal end portion of the delivery tool insert further comprises at least one locking member extending therefrom and the distal end portion of the delivery tool further comprises at least one locking recess defined therein, the locking member configured to be secured in the at least one locking recess when aligned therewith, to lock the delivery tool insert within the lumen of the delivery tool.

5. The two-piece implantable sheet delivery device of claim 1, wherein the distal end portion of the delivery tool further comprises a slot separating the distal end portion of the delivery tool into an upper and lower jaw member, the upper and lower jaw member configured to secure a distal end portion of an implantable sheet therebetween within the slot.

6. The two-piece implantable sheet delivery device of claim 1, further comprising a pair of tie holes defined through the central portion of the elongate body of the delivery tool.

7. The two-piece implantable sheet delivery device of claim 1, wherein the distal end portion of the delivery tool further comprises a suture aperture defined therethrough, the suture aperture configured to receive a looped suture suitable for grasping when withdrawing the delivery tool from a patient.

8. The two-piece implantable sheet delivery device of claim 1, wherein the distal end portion of the delivery tool further comprises at least one crenulation extending outwardly from an outer surface of the distal end portion, the crenulation configured to engage openings in an implantable sheet when rolled thereon.

9. The two-piece implantable sheet delivery device of claim 1, wherein the pair of windows are defined in the sidewall of the central portion of the elongate body.

10. A surgical kit for hernia repair comprising:
a mesh delivery tool including an elongate body extending between a proximal end portion and distal end portion, the elongate body including a lumen extending from the proximal end portion through a central portion towards the distal end portion of the elongate body and at least one window defined in a sidewall of the elongate body, the window configured to allow access to the lumen from a side of the elongate body,
a delivery tool insert configured to be received within the lumen of the elongate body, the delivery tool insert including a proximal end portion, a distal end portion, and at least one resilient arm extending therebetween, the proximal and distal end portions of the delivery tool insert configured to be received within the lumen of the elongate body, and the at least one resilient arm configured to extend through the at least one window when aligned therewith, and
an implantable sheet including a first and second opposite face.

11. The surgical kit of claim 10, further comprising a central tie configured to connect the implantable sheet to the delivery tool, wherein the central tie is configured to pass through a pair of tie holes defined through the central portion of the elongate body of the delivery tool forming a loop inside the lumen of the delivery tool and extending away from the delivery tool through the second face of the sheet and forming a handle extending away from the opposite first face of the sheet.

12. The surgical kit of claim 10, further comprising a rolling device configured to roll the implantable sheet around the outer surface of the delivery tool.

13. The surgical kit of claim 10, further comprising an insertion member including an elongate body extending between a proximal end portion including a handle and a distal end portion including a socket, the socket configured to matingly engage a proximal end of the delivery tool insert.

14. The surgical kit of claim 10, wherein the at least one window is defined in the sidewall of the central portion of the elongate body.

* * * * *